US011051688B2

(12) United States Patent
Neal et al.

(10) Patent No.: US 11,051,688 B2
(45) Date of Patent: Jul. 6, 2021

(54) OPTICAL DIAGNOSIS USING MEASUREMENT SEQUENCE

(71) Applicant: AMO Development, LLC, Santa Ana, CA (US)

(72) Inventors: Daniel R. Neal, Tijeras, NM (US); Thomas D. Raymond, Edgewood, NM (US); Leander Zickler, Bend, OR (US)

(73) Assignee: AMO Development, LLC, Santa Ana, CA (US)

( * ) Notice: Subject to any disclaimer, the term of this patent is extended or adjusted under 35 U.S.C. 154(b) by 244 days.

(21) Appl. No.: 16/167,292

(22) Filed: Oct. 22, 2018

(65) Prior Publication Data
US 2019/0053701 A1 Feb. 21, 2019

Related U.S. Application Data

(60) Division of application No. 15/343,037, filed on Nov. 3, 2016, now Pat. No. 10,105,045, which is a (Continued)

(51) Int. Cl.
*G02C 7/04* (2006.01)
*A61B 3/10* (2006.01)
(Continued)

(52) U.S. Cl.
CPC ............ *A61B 3/0025* (2013.01); *A61B 3/103* (2013.01); *A61B 3/1015* (2013.01); *A61B 3/112* (2013.01); *G02C 7/027* (2013.01); *G02C 7/04* (2013.01)

(58) Field of Classification Search
CPC ..... A61B 3/0025; A61B 3/1015; A61B 3/103; A61B 33/112; A61B 3/14; A61B 3/107;
(Continued)

(56) References Cited

U.S. PATENT DOCUMENTS 4,540,254 A 9/1985 Humphrey
4,761,071 A 8/1988 Baron
(Continued)

FOREIGN PATENT DOCUMENTS

AU 2006200896 A1 3/2006
EP 1262815 A2 12/2002
(Continued)

OTHER PUBLICATIONS

Chalita M.R., et al., "Wavefront Analysis in Post-Lasik Eyes and Its Correlation with Visual Symptoms, Refraction, and Topography," Ophthalmology, Elsevier Inc., 2004, vol. 111 (3), pp. 447-453.
(Continued)

*Primary Examiner* — Brandi N Thomas
(74) *Attorney, Agent, or Firm* — Johnson & Johnson Surgical Vision, Inc.

(57) ABSTRACT

Devices, systems, and methods that facilitate optical analysis, particularly for the diagnosis and treatment of refractive errors of the eye. An optical diagnostic method for an eye includes obtaining a sequence of aberration measurements of the eye, identifying an outlier aberration measurement of the sequence of aberration measurements, and excluding the outlier aberration measurement from the sequence of aberration measurements to produce a qualified sequence of aberration measurements. The sequence of aberrations measurements can be obtained by using a wavefront sensor. An optical correction for the eye can be formulated in response to the qualified sequence of aberration measurements.

24 Claims, 20 Drawing Sheets

Related U.S. Application Data continuation of application No. 12/909,756, filed on Oct. 21, 2010, now Pat. No. 9,504,376.

(60) Provisional application No. 61/289,324, filed on Dec. 22, 2009.

(51) Int. Cl.
*A61B 3/00* (2006.01)
*G02C 7/02* (2006.01)
*A61B 3/103* (2006.01)
*A61B 3/11* (2006.01)

(58) Field of Classification Search
CPC .. A61B 3/12; A61B 3/15; A61B 3/102; A61B 3/1035; A61B 3/113; A61B 5/0002; G02C 7/027; G02C 7/04; A61F 2009/00848; A61F 2009/00872; A61F 2009/00846; A61F 2009/00855; A61F 2009/00863; A61F 2009/00882; A61F 9/008; A61F 2009/00895; A61F 9/00804; A61F 9/00806
See application file for complete search history.

(56) References Cited

U.S. PATENT DOCUMENTS

| | | | |
|---|---|---|---|
| 4,995,716 | A | 2/1991 | Warnicki et al. |
| 5,406,342 | A | 4/1995 | Jongsma |
| 5,491,524 | A | 2/1996 | Hellmuth et al. |
| 6,004,313 | A | 12/1999 | Shimmick et al. |
| 6,116,738 | A | 9/2000 | Rorabaugh |
| 6,280,435 | B1 | 8/2001 | Odrich et al. |
| 6,396,069 | B1 | 5/2002 | MacPherson et al. |
| 6,550,917 | B1 | 4/2003 | Neal et al. |
| 6,663,619 | B2 | 12/2003 | Odrich et al. |
| 7,044,602 | B2 | 5/2006 | Chernyak |
| 7,168,807 | B2 | 1/2007 | Chernyak et al. |
| 7,175,278 | B2 | 2/2007 | Chernyak et al. |
| 7,261,412 | B2 | 8/2007 | Somani et al. |
| 7,293,873 | B2 | 11/2007 | Dai et al. |
| 7,320,517 | B2 | 1/2008 | Dai et al. |
| 7,331,674 | B2 | 2/2008 | Dai |
| 7,387,387 | B2 | 6/2008 | Dai |
| 7,413,566 | B2 | 8/2008 | Yee |
| 7,434,936 | B2 | 10/2008 | Dai et al. |
| 7,475,986 | B2 | 1/2009 | Dai et al. |
| 7,478,907 | B2 | 1/2009 | Somani et al. |
| 7,513,620 | B2 | 4/2009 | Dai et al. |
| 7,988,290 | B2 | 8/2011 | Campbell et al. |
| 8,201,941 | B2 | 6/2012 | Choo et al. |
| 2003/0086057 | A1 | 5/2003 | Cleveland |
| 2003/0086063 | A1 | 5/2003 | Williams et al. |
| 2004/0054356 | A1 | 3/2004 | Odrich et al. |
| 2004/0143246 | A1 | 7/2004 | Maeda et al. |
| 2004/0257530 | A1 | 12/2004 | Chernyak et al. |
| 2004/0263785 | A1 | 12/2004 | Chernyak |
| 2005/0261752 | A1 | 11/2005 | Chernyak |
| 2006/0215113 | A1 | 9/2006 | Chernyak |
| 2007/0008491 | A1 | 1/2007 | Polland et al. |
| 2007/0201001 | A1 | 8/2007 | Dai |
| 2007/0273828 | A1 | 11/2007 | Polland et al. |
| 2008/0291395 | A1 | 11/2008 | Dai et al. |
| 2008/0309870 | A1 | 12/2008 | Chernyak |
| 2009/0000628 | A1 | 1/2009 | Somani et al. |
| 2009/0036981 | A1 | 2/2009 | Yee |
| 2009/0161090 | A1* | 6/2009 | Campbell ............. A61B 3/107 356/3 |

FOREIGN PATENT DOCUMENTS

| | | |
|---|---|---|
| EP | 1316287 A2 | 6/2003 |
| EP | 1985269 A1 | 10/2008 |
| JP | 2010135832 A | 6/2010 |
| WO | 02088830 A1 | 11/2002 |
| WO | 2004113958 A2 | 12/2004 |
| WO | 2007038662 A2 | 4/2007 |

OTHER PUBLICATIONS

European Search Report for Application No. EP16165941, dated Sep. 27, 2016, 13 pages.
International Search Report and Written Opinion for Application No. PCT/US2010/061743, dated Jun. 28. 2011, 16 pages.
International Search Report for Application No. PCT/US2004/18906, dated May 17, 2005, 1 page.
Partial European search report for Application No. EP16165941,dated Jul. 11, 2016, 8 pages.

* cited by examiner

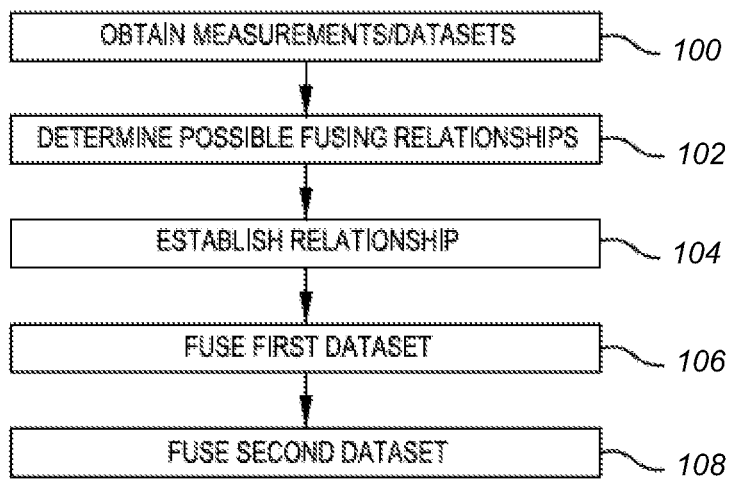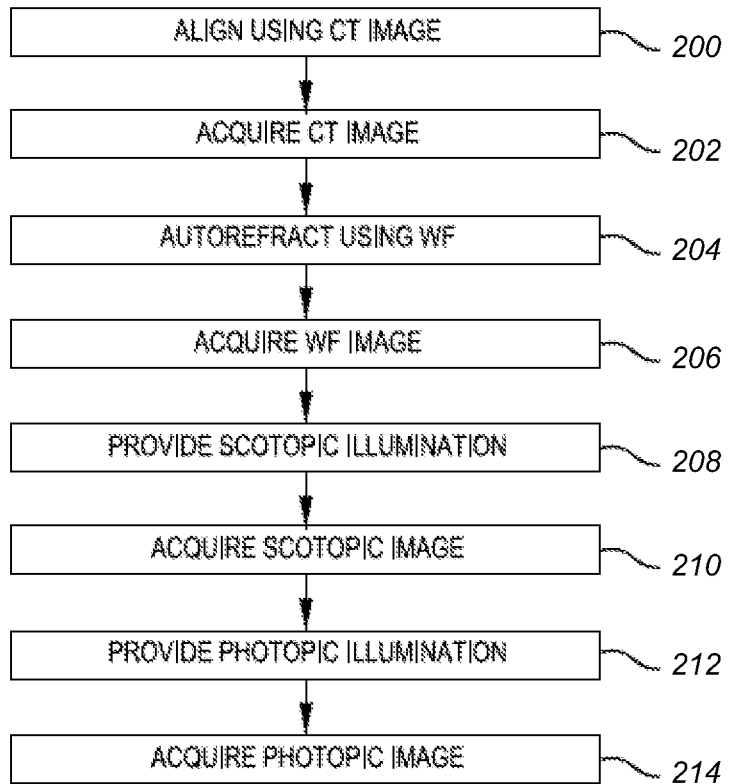

FIG. 11
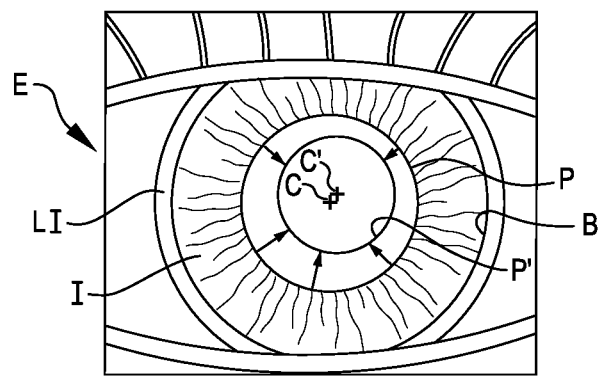
FIG. 12
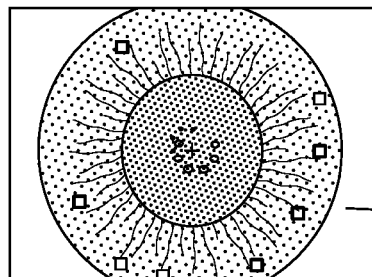
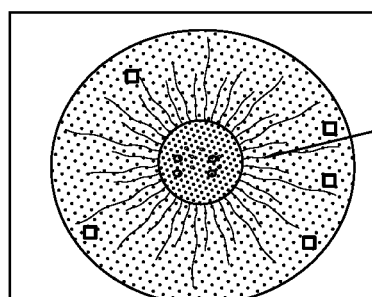
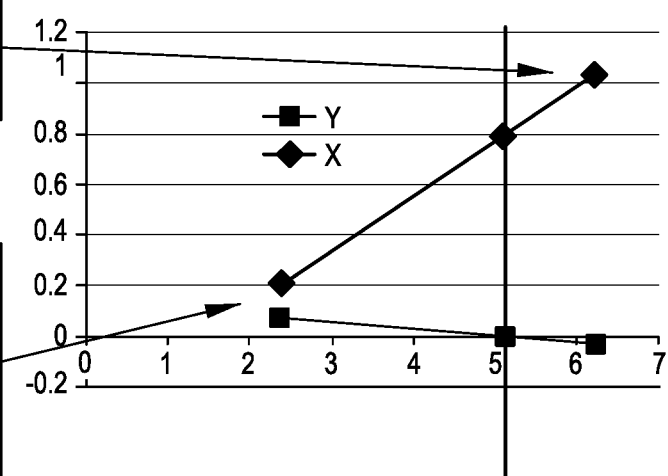

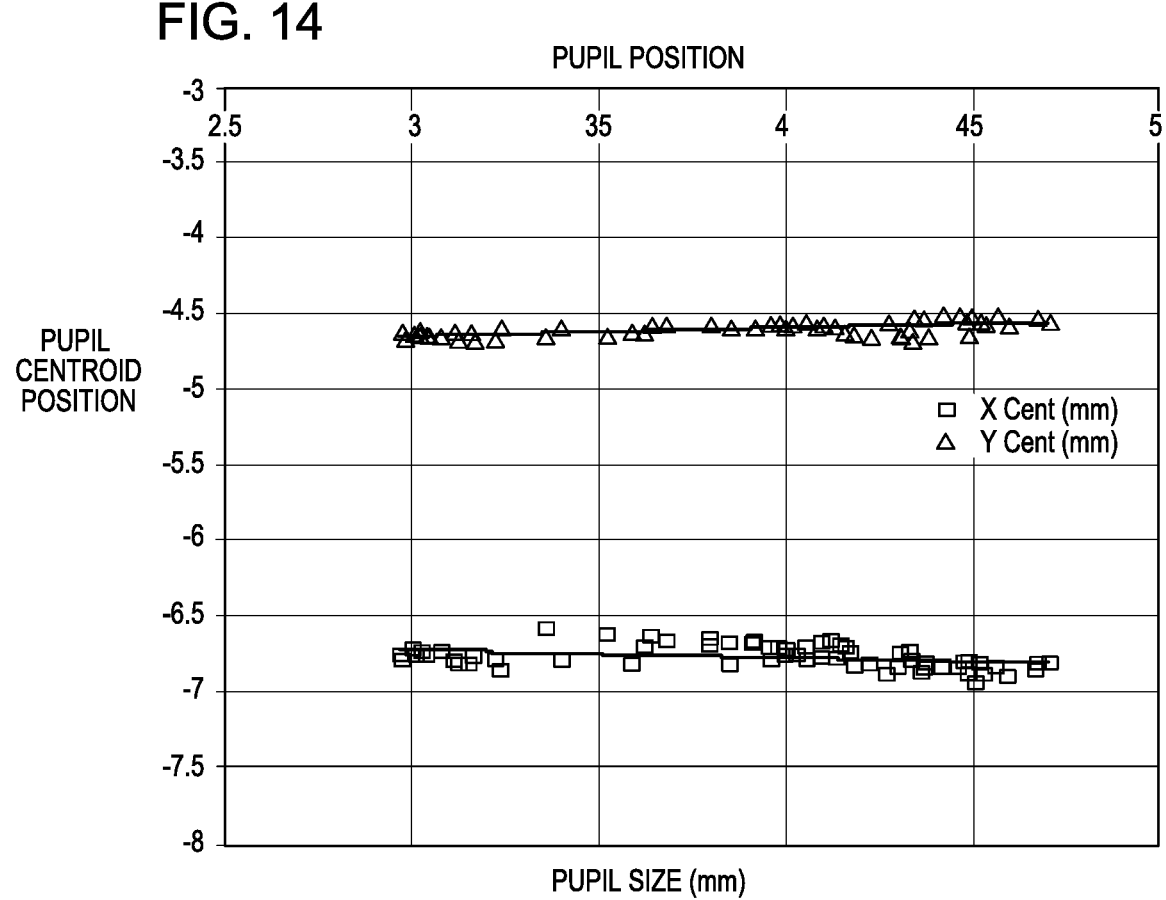

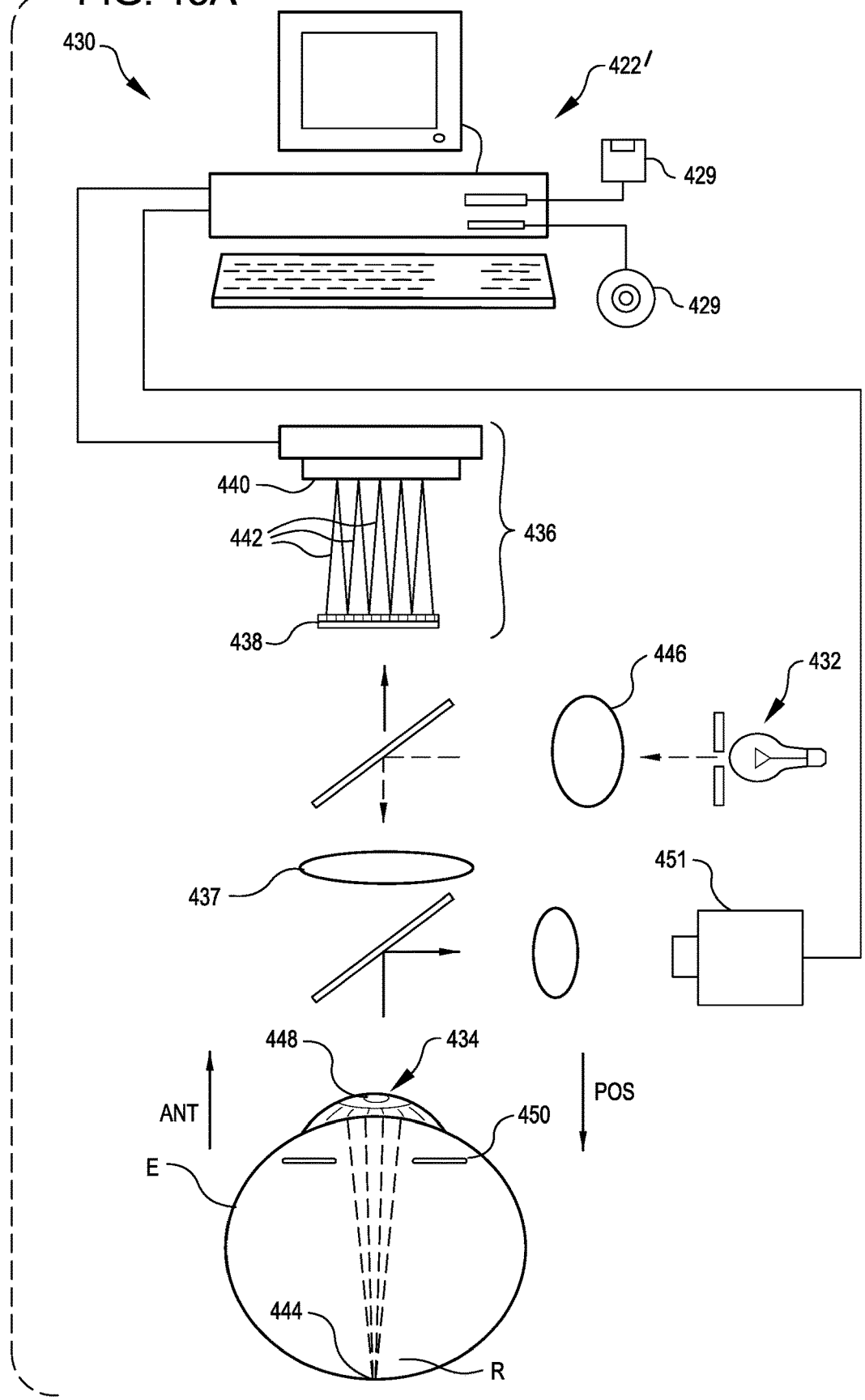

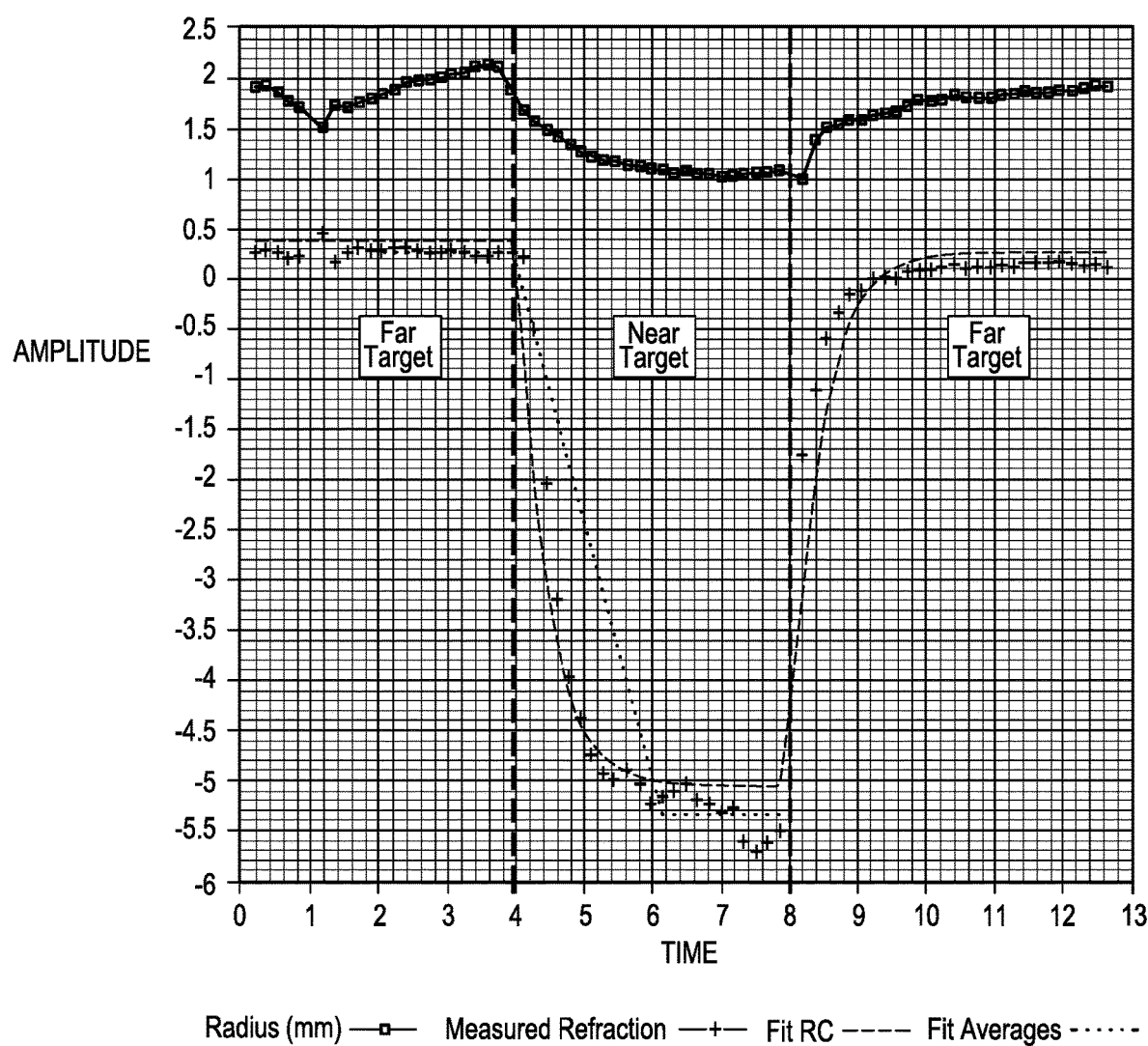

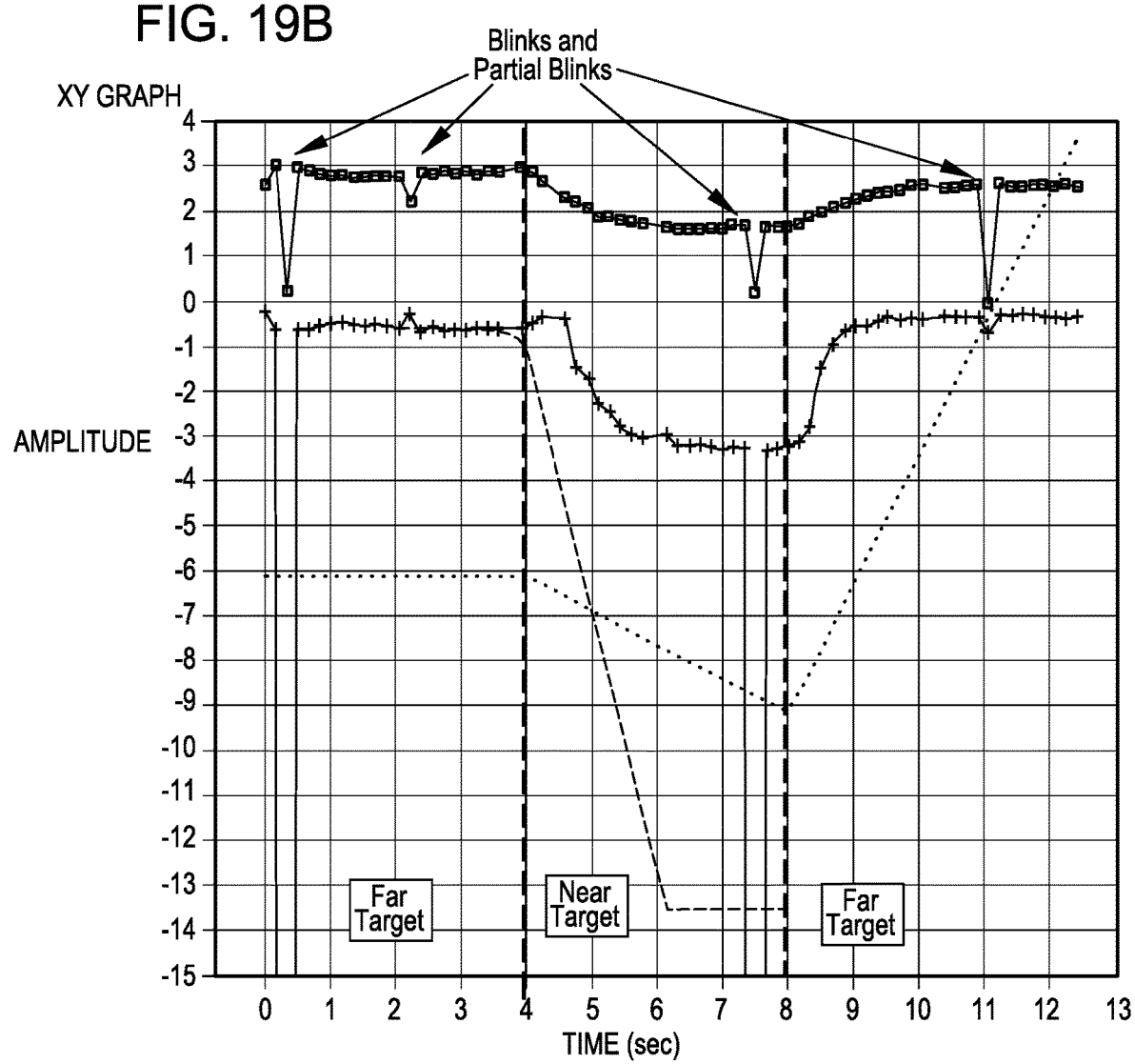

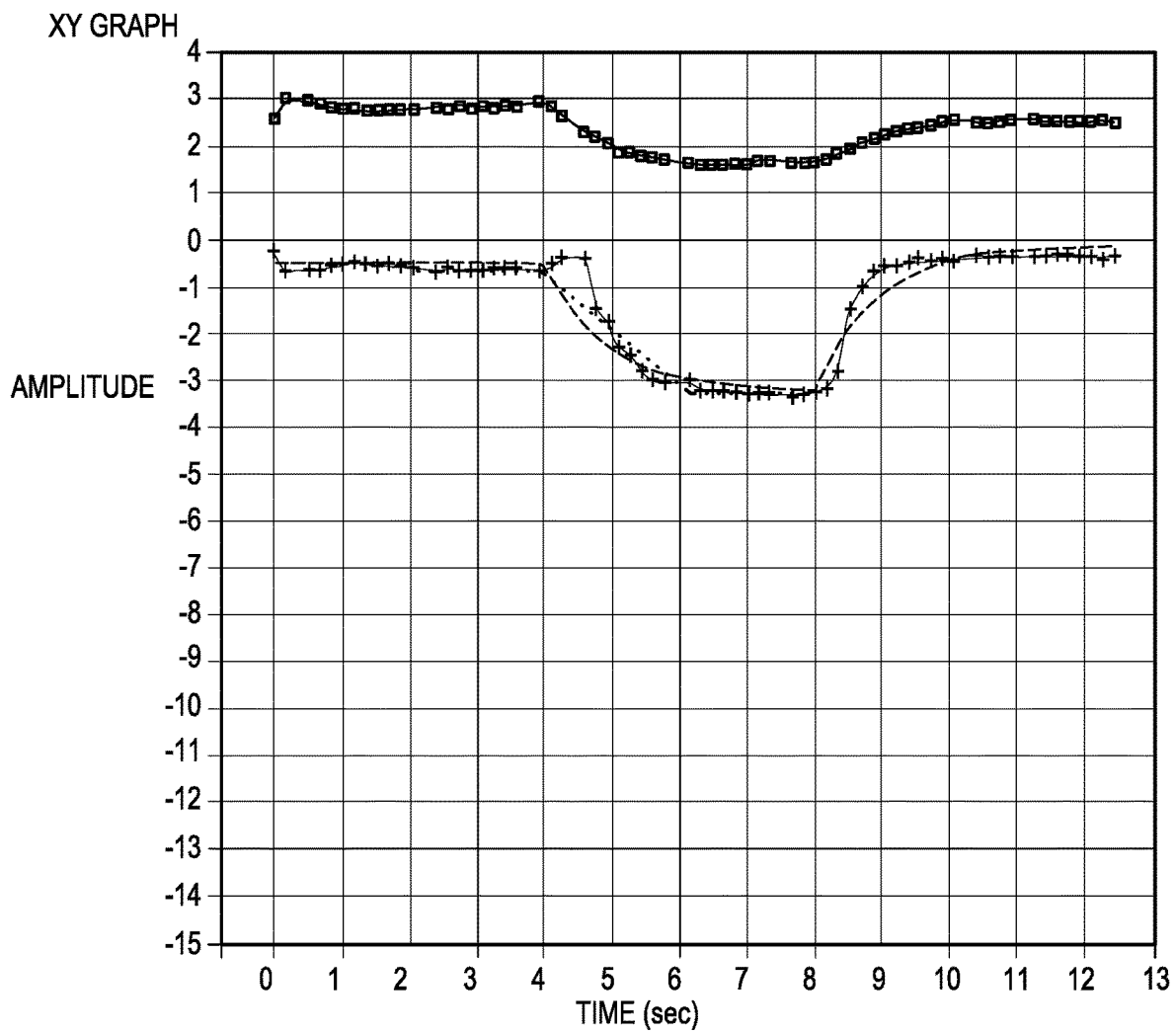

FIG. 20C
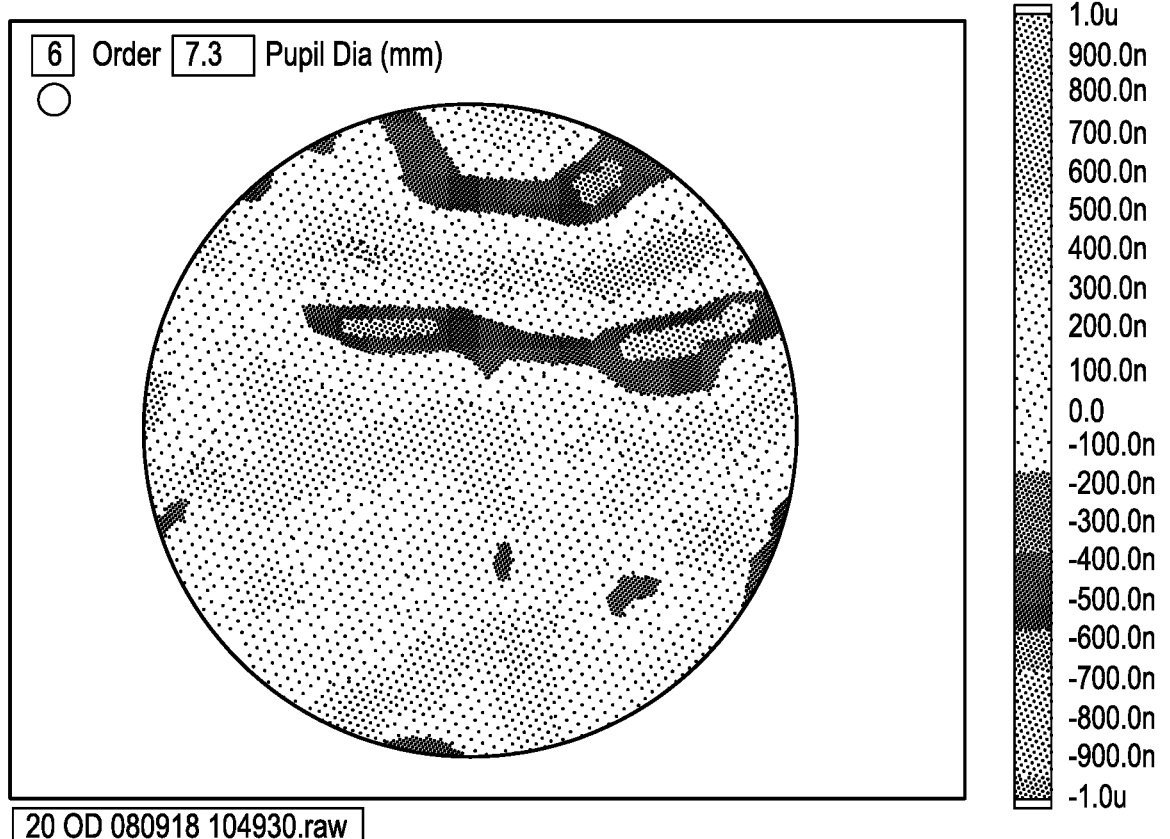
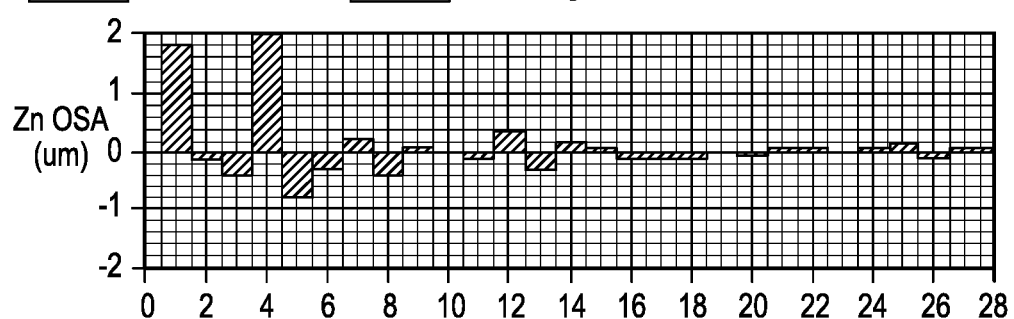

OPTICAL DIAGNOSIS USING MEASUREMENT SEQUENCE

CROSS-REFERENCES TO RELATED APPLICATIONS

This application is a divisional of and claims priority to U.S. patent application Ser. No. 15/343,037, filed Nov. 3, 2016, which is a continuation application under 35 USC § 120 of U.S. patent application Ser. No. 12/909,756, filed Oct. 21, 2010, now U.S. Pat. No. 9,504,376, which claims the benefit of U.S. Provisional Application No. 61/289,324, filed Dec. 22, 2009, the entire disclosures of the above applications are hereby incorporated herein by reference.

BACKGROUND

The present application relates generally to optical diagnosis using aberration measurements, and relates more particularly to the use of one or more sequences of aberration measurements to produce an optical diagnosis. In many embodiments, a sequence of aberrations measurements are obtained and used to quantify the aberrations of an eye. The quantified aberrations are then used to produce an optical diagnosis for the eye.

Known laser eye procedures generally employ an ultraviolet or infrared laser to remove a microscopic layer of stromal tissue from the cornea of the eye to alter the refractive characteristics of the eye. The laser removes a selected shape of the corneal tissue, often to correct refractive errors of the eye. Ultraviolet laser ablation results in photo-decomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, frequency multiplied solid-state lasers, and the like. Alternative vision correction techniques make use of radial incisions in the cornea, intraocular lenses, removable corneal support structures, thermal shaping, and the like.

Known corneal correction treatment methods have generally been successful in correcting standard vision errors, such as myopia, hyperopia, astigmatism, and the like. However, as with all successes, still further improvements would be desirable. Toward that end, wavefront measurement instruments are now available to measure the refractive characteristics of a particular patient's eye.

One promising wavefront measurement system is the iDESIGN ADVANCED WAVESCAN STUDIO System, which includes a Hartmann-Shack wavefront sensor assembly that may quantify higher-order aberrations throughout the entire optical system, including first and second-order sphero-cylindrical errors and third through sixth-order aberrations caused by coma and spherical aberrations. With advanced algorithms for measuring and applying the wavefront correction (e.g. Fourier or zonal), even higher spatial frequency structures can be corrected, providing that adequate registration can be maintained between the intended correction and its application in a practical system. The wavefront measurement of the eye creates a high order aberration map that permits assessment of aberrations throughout the optical pathway of the eye, e.g., both internal aberrations and aberrations on the corneal surface. Thereafter, the wavefront aberration information may be saved and thereafter input into a computer system to compute a custom ablation pattern to correct the aberrations in the patient's eye. A variety of alternative wavefront or other aberration measurement systems may also be available Customized refractive corrections of the eye may take a variety of different forms. For example, lenses may be implanted into the eye, with the lenses being customized to correct refractive errors of a particular patient. By customizing an ablation pattern or other refractive prescription based on wavefront measurements, it may be possible to correct minor refractive errors so as to reliably provide visual acuities better than 20/20. Alternatively, it may be desirable to correct aberrations of the eye that reduce visual acuity, even where the corrected acuity remains less than 20/20.

The determination of a customized refractive correction for an eye may be complicated by the often dynamic nature of the refraction of an eye. The optical aberrations of an eye can vary with, for example, changes in viewing conditions such as viewing distance and/or illumination. Changes in aberrations due to changes in viewing distance can become especially significant as a person ages and presbyopia sets in. Even for viewing distances within an accommodation range of an eye, different accommodation levels have different levels of muscular contraction, which may result in different aberrations due to, for example, changes in the shape of the eye arising from different internal strain levels in the eye. Even changes in the moisture level of the eye (e.g., tear film) can produce changes in the aberrations of the eye.

Consequently, multiple aberration measurements may be required to accurately characterize the aberrations of an eye. Thus, improved methods and systems that use one or more sequences of aberration measurements to accurately characterize the aberrations of an eye are desirable. Likewise, improved methods and systems for determining a customized refractive correction for an eye are also desirable.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

Improved diagnostic methods and systems are provided. In many embodiments, one or more sequences of aberrations measurements are obtained using one or more viewing conditions. The aberration measurements can be registered to a common reference. Outlier measurements can be identified and excluded from consideration. By excluding outlier measurements, a resulting optical diagnosis may more accurately address non-transient aberrations of the eye without introducing diagnosis errors associated with transient aberration measurements. The outlier measurements can be identified by processing a sequence of aberration measurements and/or by processing one or more corresponding sequences of component aberrations of the eye.

In many embodiments, statistically-significant component aberrations of the eye are determined by analyzing a sequence of aberrations measurements. Each aberration measurement of the sequence can be used to determine component aberrations that, when combined, approximate the combined aberrations of the eye for that measurement. Each of the resulting series of component aberrations can be analyzed to quantify how any particular component aberration changes over time. In many embodiments, the eye is subjected to different viewing conditions during the sequence of aberration measurements so that the effect of the different viewing conditions on the component aberrations can be determined. The determination of how the component aberrations change over time, and change with respect to different viewing conditions, provides data that can be used to select an optical correction for the eye. In many embodiments, one or more candidate optical corrections are evaluated relative to different viewing conditions so as to aid in the selection of an optical correction for the eye.

Thus, in a first aspect, an optical diagnostic method is provided for an eye having a pupil. The method includes obtaining a sequence of aberration measurements of the eye, identifying an outlier aberration measurement of the sequence of aberration measurements, and excluding the outlier aberration measurement from the sequence of measurements to produce a qualified sequence of aberration measurements. In many embodiments, the sequence of aberration measurements is obtained by using a wavefront sensor. The qualified sequence of aberration measurements can be used to formulate an optical correction for the eye.

In many embodiments, the sequence of aberration measurements and/or the qualified sequence of aberration measurements are registered by using a location of the eye. For example, the method can include determining a relationship between a size of the pupil and a location of the pupil, determining a plurality of sizes of the pupil corresponding to the sequence of aberration measurements, and registering the sequence of aberration measurements with a location of the eye by using the plurality of pupil sizes and the relationship.

In many embodiments, the sequence of aberration measurements and/or the qualified sequence of measurements are registered with an orientation of the eye (e.g., rotation about an optical axis of the eye). For example, the method can include measuring a plurality of orientations of the eye corresponding to the sequence of aberration measurements. And the aberration measurements can be registered with an orientation of the eye by using the measured orientations. The orientations of the eye can be measured, for example, by measuring a position of at least one of a natural feature of the eye (e.g., limbus, blood vessel(s) on the sclera, edge of iris) or an artificial reference mark added to the eye (e.g., a physical mark placed on the sclera).

The method can include identifying statistically-significant component aberrations of the eye. For example, the method can include determining a sequence of coefficients corresponding to a component aberration of the eye in response to at least one of the sequence of aberration measurements or the qualified sequence of aberration measurements, and processing the sequence of coefficients to determine whether the component aberration is statistically significant.

Identifying an outlier aberration measurement can be accomplished in various ways. For example, a sequence of coefficients corresponding to a component aberration of the eye can be processed to identify an outlier aberration measurement by, for example, detecting one or more coefficients of the sequence that deviate significantly from the prevailing trend of the sequence of coefficients. Post-blink aberration measurements that follow a blink of the eye by less than a predetermined amount of time can be identified as outlier measurements and can then be excluded or considered for exclusion. Identifying a blink can include at least one of detecting a radius of the pupil that is less than a predetermined value, detecting a rate of change of the pupil that is greater that a predetermined rate, or detecting a radius of the pupil that is inconsistent with a linear interpolation based on nearby qualified radius measurements of the pupil. An outlier measurement can be identified by verifying that the sphere equivalent refraction (SEQ) of the eye that is outside a predetermined range. An outlier measurement can also be identified by verifying that the rate of change of SEQ of the eye based on temporally proximate measurements is greater than a predetermined rate. An outlier measurement can also be identified by verifying that the SEQ of the eye for a measurement while viewing a far target differs from a manifest refraction of the eye by more than a predetermined value. An outlier measurement can also be identified by verifying that the SEQ of the eye for a measurement while viewing a near viewing target that differs from a manifest refraction of the eye minus a stimulus corresponding to the near viewing target by more that a predetermined value. An outlier measurement can also be identified by identifying a measurement having a first wavefront fit error (WFFE) for the eye that exceeds a second WFFE of the eye by more than a predetermined amount.

In many embodiments, the eye is subjected to different viewing conditions during the sequence of aberration measurements. The viewing conditions can include, for example, different illumination levels (e.g., a daytime illumination level, a nighttime illumination level). In many embodiments, a change of viewing condition induces an accommodation of the eye. In many embodiments, statistically-significant component aberrations of the eye are determined and quantified for one or more viewing conditions.

In many embodiments, the performance of a candidate correction for the eye is determined over different viewing conditions. For example, the method can further include determining a performance of a candidate optical correction for the eye over a plurality of the viewing conditions by using a merit function that assesses the candidate optical correction relative to the plurality of the viewing conditions. In many embodiments, the merit function includes at least one factor to account for a relative importance of at least one viewing condition. In many embodiments, the performance of the candidate correction is determined by assessing the candidate optical correction relative to the plurality of viewing conditions over a portion of the eye corresponding to a pupil size of the eye and a pupil location of the eye for the viewing condition.

In many embodiments, a prescriptive optical correction for the eye is determined in response to the performances of a number of candidate optical corrections for the eye. For example, the method can include determining a performance of each of a number of candidate optical corrections for the eye over each of a number of the viewing conditions, and determining a prescriptive optical correction for the eye in response to the determined performances for the candidate optical corrections.

In another aspect, a method is provided for configuring a contact lens for an eye. The method includes obtaining a corrective prescription for the eye, measuring a sequence of positions of a contact disposed on the eye relative to the eye, determining a statistical dispersion of the sequence of positions, and determining an optical correction to incorporate into the contact lens based on the corrective prescription and the statistical dispersion.

In many embodiments, a performance of a contact lens having a candidate correction is determined over a number of relative positions between the contact lens and the eye. In many embodiments, the relative positions used are based on the statistical dispersion. In many embodiments, a performance of the contact lens is also determined for a number of viewing conditions for at least one of the relative positions.

In many embodiments, the contact lens is configured by determining which high-order corrections to exclude from the optical correction to be incorporated into the contact lens. For example, in many embodiments, the corrective prescription for the eye includes low-order and high-order corrections; and the step of determining an optical correction to incorporate includes excluding at least one high-order correction based on the statistical dispersion.

In another aspect, an optical diagnostic system is provided for an eye having a pupil. The system includes a sensing device for sensing aberrations of the eye for each of a sequence of aberrations measurements of the eye, and a computer coupled with the sensing device. The computer includes a processor and a computer readable medium comprising instructions executable by the processor to identify an outlier aberration measurement of the sequence of aberration measurements of the eye and exclude the outlier aberration measurement from the sequence of aberration measurements to produce a qualified sequence of aberration measurements. In many embodiments, the sensing device comprises a wavefront sensor. In many embodiments, the wavefront system determines a plurality of refractive coefficients corresponding to sensed aberrations of the eye for each measurement of the sequence of measurements. In many embodiments, the computer readable medium further includes instructions executable by the processor for determining a plurality of refractive coefficients corresponding to sensed aberrations of the eye for each measurement of the sequence of measurements. In many embodiments, the instructions are executable by the processor to formulate an optical correction for the eye in response to the qualified sequence of aberration measurements.

In many embodiments, the system registers the sequence of aberration measurements with a location of the eye. For example, the computer readable medium can store a relationship between a size of the pupil and the location of the pupil, and can further include instructions executable by the processor for determining a plurality of sizes of the pupil corresponding to the sequence of aberration measurements, and registering the sequence of aberration measurements with a location of the eye by using the plurality of pupil sizes and the relationship.

In many embodiments, the system registers the sequence of aberration measurements with an orientation of the eye. For example, the computer can further include an input receiving data from which eye orientations corresponding to the sequence of aberration measurements can be generated.

And the computer readable medium can further include instructions executable by the processor for determining orientations of the eye in response to the eye orientation data, and registering the aberration measurements with an orientation of the eye by using the determined orientations. In many embodiments, the system further includes a measurement device coupled with the input and measuring a position of at least one of a natural feature of the eye or an artificial reference mark added to the eye so as to generate the eye orientation data.

The system can identifying an outlier aberration measurement in various ways. For example, a sequence of coefficients corresponding to a component aberration of the eye can be processed to identify a outlier aberration measurement by, for example, detecting one or more coefficients of the sequence that deviate significantly from the prevailing trend of the sequence of coefficients. Post-blink aberration measurements that follow a blink of the eye by less than a predetermined amount of time can be identified as outlier measurements and can then be excluded or considered for exclusion. Identifying a blink can include at least one of detecting a radius of the pupil that is less than a predetermined value, detecting a rate of change of the pupil that is greater that a predetermined rate, or detecting a radius of the pupil that is inconsistent with a linear interpolation based on nearby qualified radius measurements of the pupil. An outlier measurement can be identified by identifying a sphere equivalent refraction (SEQ) of the eye that is outside a predetermined range. An outlier measurement can be identified by identifying a rate of change of SEQ of the eye that is greater than a predetermined rate. An outlier measurement can be identified by identifying a SEQ of the eye for a measurement corresponding to viewing a far viewing target that differs from a manifest refraction of the eye by more than a predetermined value. An outlier measurement can be identified by identifying a SEQ of the eye for a measurement corresponding to viewing a near viewing target that differs from a manifest refraction of the eye minus a stimulus corresponding to the near viewing target by more that a predetermined value. An outlier measurement can be identified by identifying a measurement having a first wavefront fit error (WFFE) for the eye that exceeds a second WFFE of the eye by more than a predetermined amount.

In many embodiments, the system includes an input receiving data from which a plurality of viewing conditions imposed upon the eye during the sequence of aberrations measurements can be determined. And the computer readable medium can further includes instructions executable by the processor for determining the plurality of viewing conditions and storing the plurality of viewing conditions in the computer readable medium. The viewing conditions can include different illumination levels, for example, a daytime illumination level and/or a nighttime illumination level. In many embodiments, a change from one of the viewing conditions to another of the viewing conditions induces an accommodation of the eye. In many embodiments, statistically-significant component aberrations of the eye are determined and quantified for one or more viewing conditions.

In many embodiments, the system determines a performance of a candidate correction for the eye over different viewing conditions. For example, the computer readable medium can further include instructions executable by the processor for determining a performance of a candidate optical correction for the eye over a plurality of the viewing conditions by using a merit function that assesses the candidate optical correction relative to the plurality of the viewing conditions. In many embodiments, the merit function includes at least one factor to account for a relative importance of at least one viewing condition. In many embodiments, the performance of the candidate correction is determined by assessing the candidate optical correction relative to the plurality of viewing conditions over a portion of the eye corresponding to a pupil size of the eye and a pupil location of the eye for the viewing condition.

In many embodiments, a prescriptive optical correction for the eye is determined in response to the performances of a number of candidate optical corrections for the eye. For example, the computer readable medium can further include instructions executable by the processor for determining a performance of each of a plurality of candidate optical corrections for the eye over each of a plurality of the viewing conditions, and determining a prescriptive optical correction for the eye in response to the determined performances for the candidate optical corrections.

For a fuller understanding of the nature and advantages of the present invention, reference should be made to the ensuing detailed description and accompanying drawings.

BRIEF DESCRIPTION OF THE DRAWINGS

FIG. 4 is a flow chart showing steps for aligning, registering, or fusing data in accordance with an embodiment FIG. 5 is a flow chart showing a measurement sequence that may be used to acquire eye measurements with first and second measuring instruments in accordance with an embodiment.

FIG. 11 is a diagram representing an eye and showing that as the pupil contracts, it also shifts in position.

FIG. 12 schematically illustrates a relationship between pupil size and location as derived from images of the eye under scotopic/mesopic conditions and photopic conditions, and also shows determination of a wavefront sensor pupil position from a pupil size identified using wavefront aberrometry data, combined with the relationship.

FIG. 14 illustrates exemplary pupil positions for a range of pupil sizes, in accordance with many embodiments.

FIG. 15A illustrates a wavefront measurement system in accordance with many embodiments.

FIG. 19A illustrates a sequence of accommodation measurements of a young eye, in accordance with many embodiments.

FIG. 19B illustrates outlier accommodation measurements caused by blinks and partial blinks, in accordance with many embodiments.

FIG. 19C illustrates a qualified sequence of accommodation measurements obtained by excluding outlier accommodation measurements, in accordance with many embodiments.

FIG. 20C shows a difference between a zonal approximation of a wavefront surface and a $6^{th}$ order modal approximation of a wavefront surface for a wavefront measurement influenced by a tear film, in accordance with many embodiments.

DETAILED DESCRIPTION

Figure 1:
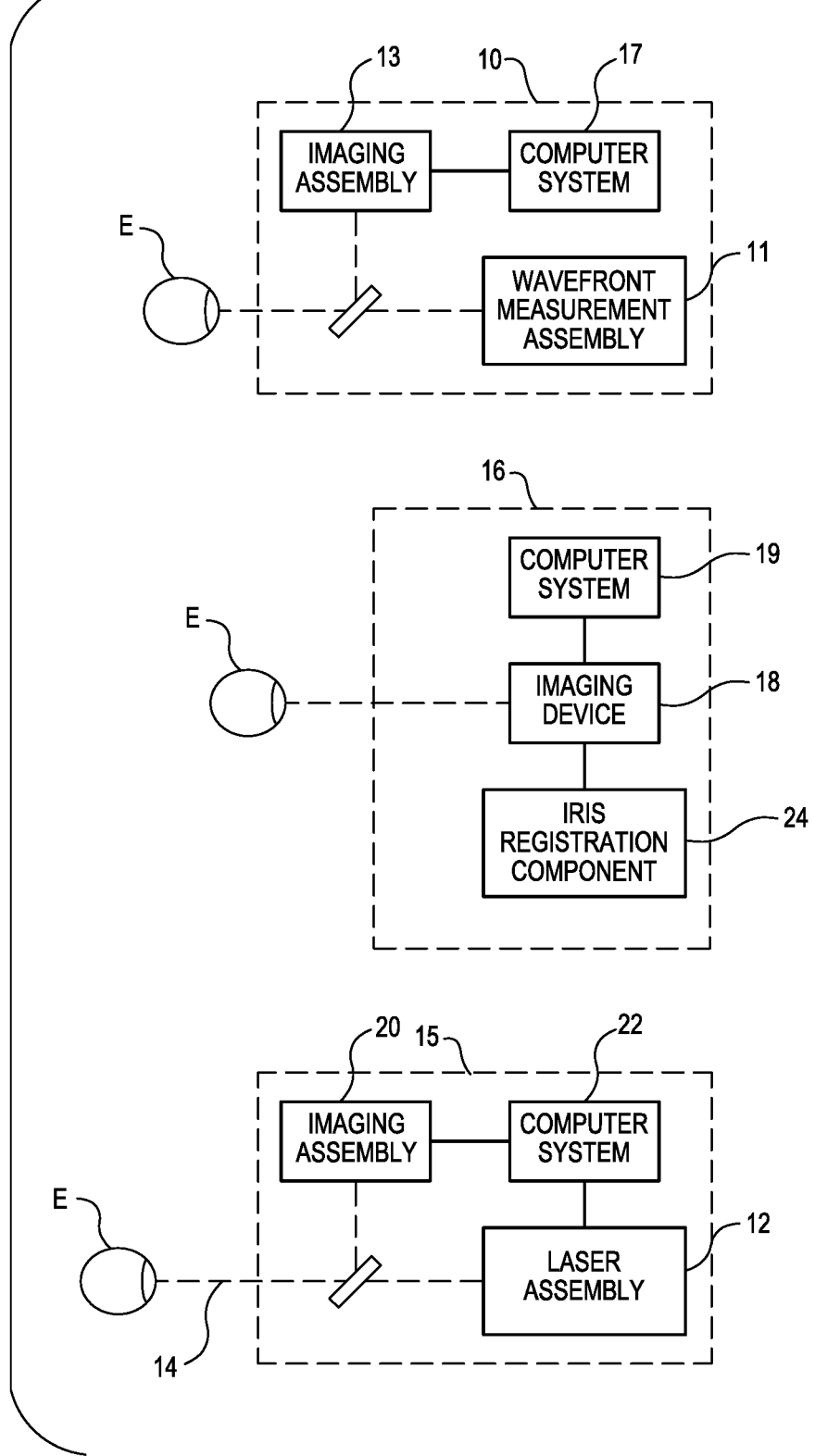
FIG. 1 schematically illustrates a simplified system of one embodiment of the present invention.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order to not obscure the embodiment being described.

Embodiments herein provide devices, systems, and methods that facilitate optical analysis, particularly for the diagnosis and treatment of refractive errors of the eye. Embodiments of the invention facilitate the use of multi-modal diagnostic instruments and instrument systems, making it easier to acquire and fuse (e.g., synthesize) data from different measurements of the eye. For example, wavefront aberrometry may be fused with corneal topography, optical coherence topography and wavefront, optical coherence topography and topography, pachymetry and wavefront, etc. While some of these different optical datasets may be obtained simultaneously, it is often difficult and/or disadvantageous to attempt to acquire the images or other data at exactly the same time. Embodiments herein permit registration of multiple datasets from measurements regardless of the sequence the measurements were taken.

Acquiring and fusing data from different measurements of the eye have significant potential advantages. For example, wavefront aberrometry and corneal topography may be used separately to each provide a beneficial refractive prescription, but the registration and combination of information from both measurements may provide improved refractive prescriptions and the like. These prescriptions may be used, for example, with a laser surgery system.

Additional embodiments herein provide for the determination of statistically-significant aberration of an eye by analyzing a sequence of aberration measurements of the eye. The statistically-significant aberrations can be determined for different viewing conditions including, for example, different illumination levels and different viewing distances. The statistically-significant aberrations can be used to formulate one or more candidate optical corrections. And the one or more candidate corrections can be evaluated with respect to the aberrations of the eye for one or more viewing conditions. A merit function can be used to rate the performance of a candidate correction. And the merit function can include one or more factors to account for a relative importance of at least one viewing condition.

The determination of statistically-significant aberrations has significant potential advantages. For example, by distinguishing between statistically-significant and non-significant aberrations, the resulting correction may more accurately correct aberrations of the eye by avoiding the correction of transient aberrations arising from transient dynamics of the eye. Determining statistically-significant aberrations for different viewing conditions provides data that enables the selection of an optical correction that provides a more optimum compromise with regard to the various viewing conditions faced by a person (e.g., nighttime, daytime, distance vision, close vision, etc.).

Additional embodiments herein provide for the configuration of a contact lens to reflect observed levels of relative movement between the contact lens and an eye. A sequence of positions of a contact relative to the eye can be measured and analyzed to determine a statistical dispersion of the relative positions. The resulting statistical dispersion can be used to select which optical corrections to include in the contact lens.

Such a configuration approach for a contact lens has significant potential advantages. For example, a common current practice for configuring a contact lens is to only include low-order corrections in the contact lens (e.g., first and second order corrections). By determining the dispersion of the relative movements, it may be possible to include higher-order corrections into the contact lens. For example, where the observed motion is between 0.5 mm and 1.0 mm, it may be possible to include third order corrections into the contact lens. Where the observed motion is less than 0.5 mm, it may be possible to include even higher-order corrections into the contact lens (e.g., fourth order, fifth order, and/or sixth order). Where higher-order corrections can be included, an improved vision correction may result.

FIG. 1 schematically illustrates a simplified system of one embodiment of the present invention. Advantageously, elements, components, subsystems, and method elements to be used in embodiments of the present invention can be taken and/or derived from a number of known structures and methods. Exemplary constituent elements may include structures and/or techniques found in or derived from those of U.S. Pat. No. 7,044,602 in the name of Chernyak and entitled "Methods and Systems for Tracking a Torsional Orientation and Position of an Eye"; US Patent Application Publication No. 2004/0263785 in the name of Chernyak and entitled "Methods and Devices for Registering Optical Measurement Datasets of an Optical System"; and/or US Patent Application Publication No. 2006/0215113 in the name of Chernyak and entitled "Pupilometer for Pupil Center Drift and Pupil Size Measurements at Differing Viewing Distances"; the full disclosures of which are incorporated herein by reference. Alternative embodiments may use, for example, different commercially available pupil location and/or size measurement structures, different iris or other natural or artificial rotational markers, or the like, so that not all aspects of the present invention will necessarily be limited to these particular components.

In the embodiment shown in FIG. 1, the system includes a first measurement instrument 10, a second measurement instrument 16, and a laser system 15. In an embodiment, the first measurement instrument 10 is a wavefront measurement device 10 that measures aberrations and other optical characteristics of an ocular or other optical tissue system. The data from such a wavefront measurement device may be used to generate an optical surface from an array of optical gradients. It should be understood that the optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients should correct the optical tissue system. As used herein terms such as "an optical tissue surface" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium to be displaced and expose the underlying stroma during a LASIK procedure).

The second measurement instrument 16 may include a corneal topographer. Corneal topographer 16 may be used to diagnose and examine the corneal surface. Corneal topographer 16 typically includes an imaging device 18, such as a frame grabber that takes images of the cornea. The images obtained by the frame grabber are analyzed by a computer system 19, and the computer system may generate one or more graphical and/or tabular outputs, including three dimensional topographical maps. Corneal topographer 16 may determine the contours of the corneal surface by measuring the elevations and depressions in the corneal surface. One example of a corneal topographer 16 utilizes a laser, LED or other light source that maps a series of dots on the surface of the cornea. Reflected light rays of the dots are reflected to a sensor, which in turn provides data to the computer system 19 regarding the reflected dots. The computer system 19 forms a corneal elevation map from the data. An example of such a system, sometimes called a full gradient topographer, is the iDESIGN ADVANCED WAVESCAN STUDIO System, which is at least partially described in co-pending U.S. patent application Ser. No. 12/347,909, filed Dec. 31, 2008, and entitled "Systems and Methods for Measuring the Shape and Location of an Object," and which is herein incorporated by reference.

Another example of a corneal topographer is the HUMPHREY ATLAS Corneal Topographer, from Zeiss Humphrey Systems, of Dublin, Calif., which is an instrument that uses Placido disk technology to generate images of the corneal surface. The ring-based corneal topographer 16 may be based on a method that captures the reflection of rings of light off of the surface of the cornea and measures the distortion in the reflected light. A detector (not shown) captures the reflected images and computer system 19 processes the data, and displays the information in one or more formats selected by the user. For example, corneal topographer 16 may provide an axial map (which describe the radius of the curvature of the cornea relative to optic axis), curvature maps (which portray the radius of the curvature independent of the optic axis), and/or elevation maps (which illustrate the radius relative to a reference sphere).

As can be appreciated, the full gradient topographer and the HUMPHREY ATLAS topographer are merely two examples of corneal topographers that may be used with the present invention. Other corneal topographers sold by Topcon Medical Systems, Dicon Diagnostics, Haag-Streit, Eye-Quip, Tomey Corp., Bausch & Lomb, Carl Zeiss Ophthalmic Systems, Nidek, and Laser Sight may be used with the present invention. Some systems and methods for measuring a corneal topography of an eye are described in U.S. Pat. Nos. 4,761,071, 4,995,716, 5,406,342, 6,396,069, 6,116,738, 4,540,254 and 5,491,524, the full disclosures of which are incorporated herein by reference.

In an embodiment, the corneal topographer 16 includes an iris registration component, which may include cameras and pupilometer measurement features, such as described in US Patent Application Publication No. 2006/0215113 in the name of Chernyak and entitled "Pupilometer for Pupil Center Drift and Pupil Size Measurements at Differing Viewing Distances," the full disclosure of which is incorporated herein by reference. The iris registration features may alternatively be included with the first measurement instrument 10, or as a completely separate system. In addition, although shown as two separate measurement instruments 10 and 16, the features of the first and second measurement instruments may be provided on a single system.

Furthermore, while embodiments herein focus on registering datasets of an eye from a wavefront measurement instrument, such as the first measurement instrument 10, and a corneal topographer, such as the second measurement instrument 16, embodiments of the present invention are equally applicable to registering datasets obtained by a variety of other optical measurement instruments. For example, the present invention may be used to fuse data from optical coherence topography and wavefront, optical coherence topography and topography, pachymetry and wavefront, and the like.

The laser surgery system 15 surgery system 15 includes a laser assembly 12 that produces a laser beam 14. Laser assembly 12 is optically coupled to laser delivery optics (not shown), which directs laser beam 14 to an eye E of a patient. An imaging assembly 20, such as a microscope is mounted on the delivery optics support structure to image a cornea of eye E during the laser procedure.

Laser assembly 12 generally comprises an excimer laser source, typically comprising an argon-fluorine laser producing pulses of laser light having a wavelength of approximately 193 nm. Laser assembly 12 will preferably be designed to provide a feedback stabilized fluence at the patient's eye, delivered via delivery optics. Although an excimer laser is the illustrative source of an ablating beam, other lasers may be used.

Laser assembly 12 and delivery optics will generally direct laser beam 14 to the eye E under the direction of a computer system 22. Computer system 22 will generally selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system will be under computer control of computer system 22 to affect the desired laser sculpting process so as to deliver the customized ablation profile, with the computer system ideally altering the ablation procedure in response to inputs from the optical feedback system. The feedback will preferably be input into computer system 22 from an automated image analysis system, or may be manually input into the processor by a system operator using an input device in response to a visual inspection of analysis images provided by the optical feedback system. Computer system 22 will often continue and/or terminate a sculpting treatment in response to the feedback, and may optionally also modify the planned sculpting based at least in part on the feedback.

While embodiments herein are described primarily in the context of improving diagnosis and treatment of the refractive errors of the eye using a laser eye surgery system 15, it should be understood the present invention may be adapted for use in alternative diagnosis of other optical systems, eye treatment procedures, and optical systems such as femtosecond lasers and laser treatment, infrared lasers and laser treatments, radial keratotomy (RK), scleral bands, follow up diagnostic procedures, and the like.

Figure 2:
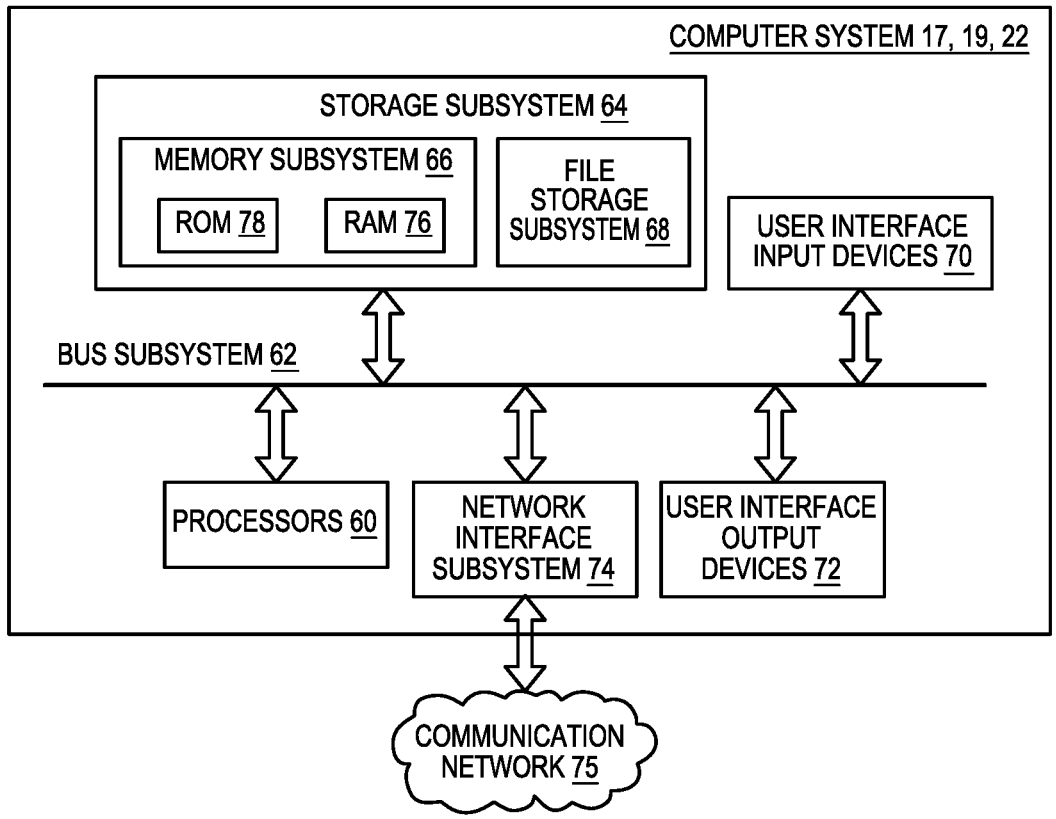
FIG. 2 is a simplified block diagram of an exemplary computer system in accordance with an embodiment.

FIG. 2 is a simplified block diagram of an exemplary computer system 17, 19, 22 in accordance with an embodiment. The computer system typically includes at least one processor 60 which communicates with a number of peripheral devices via a bus subsystem 62. These peripheral devices may include a storage subsystem 64, comprising a memory subsystem 66 and a file storage subsystem 68, user interface input devices 70, user interface output devices 72, and a network interface subsystem 74. Network interface subsystem 74 provides an interface to a communication network 75 for communication with other imaging devices, databases, or the like.

The processor 60 performs the operation of the computer systems 17, 19, 22 using execution instructions stored in the memory subsystem 66 in conjunction with any data input from an operator. Such data can, for example, be input through user interface input devices 70, such as the graphical user interface. Thus, processor 60 can include an execution area into which execution instructions are loaded from memory. These execution instructions will then cause processor 60 to send commands to the computer system 17, 19, 22, which in turn control the operation of the first measurement instrument 10, the second measurement instrument 16, and the laser system 15. Although described as a "processor" in this disclosure and throughout the claims, the functions of the processor may be performed by multiple processors in one computer or distributed over several computers.

User interface input devices 70 may include a keyboard, pointing devices such as a mouse, trackball, touch pad, or graphics tablet, a scanner, foot pedals, a joystick, a touch screen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 72 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 64 stores the basic programming and data constructs that provide the functionality of the various embodiments. For example, database and modules implementing the functionality of embodiments described herein may be stored in storage subsystem 64. These software modules are generally executed by processor 60. In a distributed environment, the software modules may be stored in a memory of a plurality of computer systems and executed by processors of the plurality of computer systems. Storage subsystem 64 typically comprises memory subsystem 66 and file storage subsystem 68.

Memory subsystem 66 typically includes a number of memories including a main random access memory (RAM) 76 for storage of instructions and data during program execution and a read only memory (ROM) 78 in which fixed instructions are stored. File storage subsystem 68 provides persistent (non-volatile) storage for program and data files, and may include a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 68.

Bus subsystem 62 provides a mechanism for letting the various components and subsystems of the computer system communicate with each other as intended. The various subsystems and components of the computer system need not be at the same physical location but may be distributed at various locations within a distributed network. Although bus subsystem 62 is shown schematically as a single bus, alternate embodiments of the bus subsystem may utilize multiple busses.

The computer system itself can be of varying types including a personal computer, a portable computer, a workstation, a computer terminal, a network computer, a module in the imaging unit, a mainframe, or any other data processing system. Due to the ever-changing nature of computers and networks, the description of the computer system depicted in FIG. 2 is intended only as a specific example for purposes of illustrating one embodiment of the present invention. Many other configurations of the computer system are possible having more or less components than the computer system depicted in FIG. 2.

Figure 3:
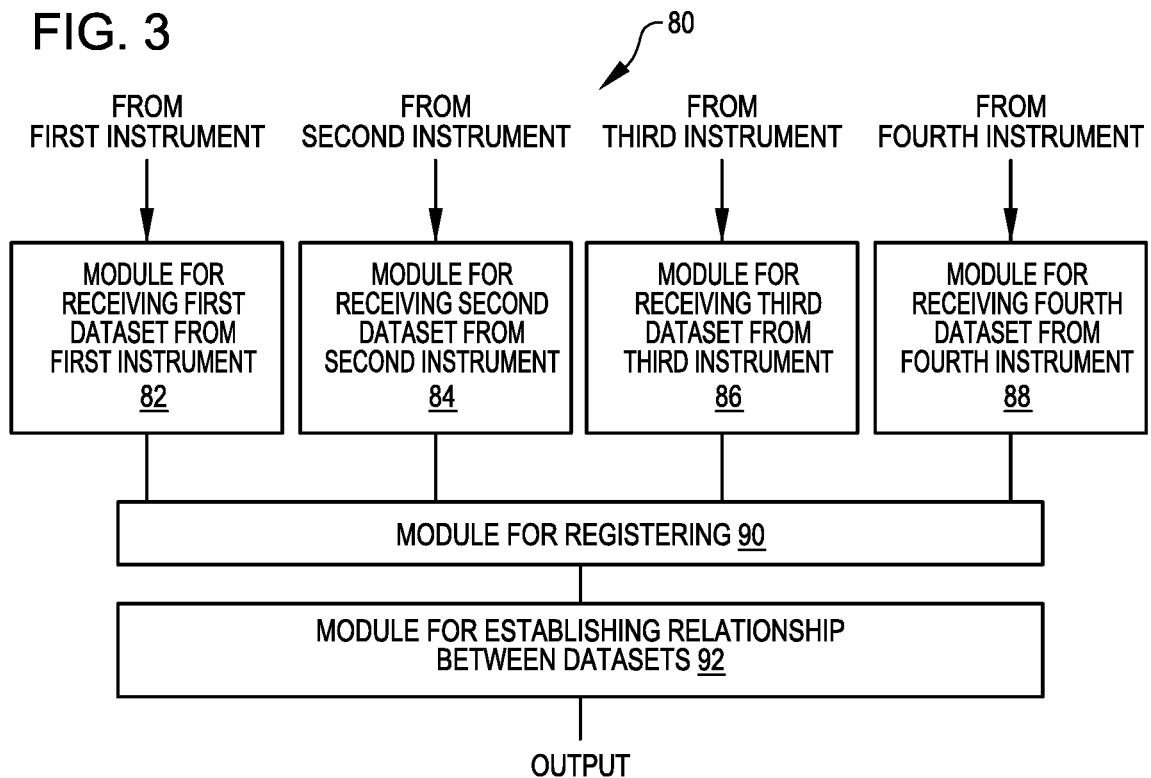
FIG. 3 schematically illustrates a plurality of modules that may carry out embodiments of the present invention.

FIG. 3 schematically illustrates a plurality of modules 80 that may carry out embodiments of the present invention. The modules 80 may be software modules, hardware modules, or a combination thereof. If the modules are software modules, the modules will be embodied on a computer readable medium and processed by a processor 60 in any of computer systems of the present invention.

A first dataset from a first instrument will be received by module 82. The first dataset is typically an optical measurement and/or image of an optical system, such as an eye. For example, in one embodiment, the optical measurement is in the form of a wavefront measurement of a patient's eye. Such a wavefront measurement may be obtained by the wavefront measurement assembly 11.

A second dataset from a second instrument is received by module 84. The second dataset is also typically an optical measurement and/or image of the same optical system. For example, in one embodiment, the second optical measurement is in the form of a corneal topographical map of the patient's eye E, from the imaging device 18.

A third and fourth modules 86, 88 receive third and fourth datasets, respectively, which, in an embodiment, are also optical measurements and/or images of an optical system, such as an eye E. As described below, these additional datasets provide information that may be used to fuse the first and second datasets, and/or may provide additional data that may be fused with the first and second datasets. Although the embodiment shown includes the two modules 86, 88, a single module may be used, and a single dataset, depending upon the information utilized to fuse the first and second datasets and/or to be fused with the first and second datasets. In an embodiment, the third dataset is an iris registration scotopic/mesopic image from the iris registration component 24. This image measures the pupil size, position and shape, and the outer iris boundary position and size in low light conditions. In an embodiment, the fourth dataset is an iris registration photopic image from the iris registration component 24. This image is used to measure the pupil size, position and shape, and the outer iris boundary position and size in bright light conditions. These images may be obtained by the iris registration component 24, for example.

The first, second, third and fourth datasets may be transmitted from the first instrument 10 and second instrument 16 over a communication network, or the datasets from each of the devices may be stored on a computer readable medium and uploaded to the computer system that processes the modules 80.

In order to take maximum advantage of the first, second, third and/or fourth datasets for diagnosis of refractive errors of the eye and for conical treatment planning, the datasets may be registered, or the data from the images fused. Consequently, the first, second, third and fourth datasets may be transmitted to a registration module 90 where one or more image processing algorithms are applied to the datasets to register the datasets.

Some measurement instruments may not produce datasets that are readily registered. Incompatibility may be based upon the fact that the two datasets are taken at different times, and/or movement of the eye may occur between measurements. To address such problems, a single measurement instrument might acquire multiple different types of ophthalmic measurements simultaneously, using synchronized cameras or the like. Although simultaneous recording might facilitate registration, it is often difficult, impossible, or undesirable to acquire the images at exactly the same time. For example, different illumination states may be desired for different types of measurements, requiring measurements be taken at different times. For example, in some ring-based measurement systems, corneal topography (CT) illumination may be incompatible with iris registration imaging via wavefront, because wavefront may benefit from a largest pupil size (thus scotopic), but the corneal topography illumination shrinks the size of the pupil.

In accordance with an embodiment, a relationship module 92 is provided that allows datasets of the eye to be registered, whether taken by a single measurement instrument having a single eye measurement location, or by separate measurement devices or the like having separate eye measurement locations. Moreover, in accordance with an embodiment, the multiple measurements may be taken at different moments in time, and the measurements may be registered together despite movement of the eye between the eye measurements. Thus, embodiments described herein may significantly facilitate use of the combination of some eye measurement systems not typically combinable for simultaneous measurement, and thus enhance measurement accuracy.

As described in more detail below, the relationship module 92 determines proper registration and alignment between multiple data types so that these data may be used together (fused) to produce a combined measurement. In embodiments, the relationship module 92 removes limitations of measurement sequence and illumination in the registration process. In accordance with one embodiment, as further described below, the relationship module 92 identifies, and corrects for, changes in the pupil size, position and shape during the measurement process, and thereby maintains accurate alignment between the various measurements.

FIG. 4 is a flow chart showing steps for registering or fusing data in accordance with an embodiment. Beginning at step 100, the first and second measuring instruments 10 and 16 are used to acquire measurements of the eye. The measurements include image datasets. A sequence for acquiring measurements is described together with FIG. 5.

FIG. 5 is a flow chart showing a measurement sequence that may be used to acquire eye measurements with the first and second measuring instruments 10, 16 in accordance with an embodiment. Beginning at step 200, the second measuring instrument 16 is aligned using the corneal topography image. At step 202, the corneal topography image is acquired.

At step 204, the first measuring instrument 10 is used to auto refract, for example using the wavefront measurement assembly 11. At step 206, a wavefront image is acquired.

At step 208, illumination is set to take a scotopic image. At step 210, the scotopic image is acquired. At step 212, illumination is set to take a photopic image, and at step 214, after a delay to allow the pupil to contract, the photopic image is acquired.

After the sequence in FIG. 5, the system has four different images. Acquisition of these images does not have to be in the sequence provided in FIG. 5. In addition, the images need not be taken at the same time, and they may have different illumination from image to image. A time difference between measurements may result in the eye moving to a different location and a change in illumination may result in the pupil changing in size and relative position.

Figure 6:
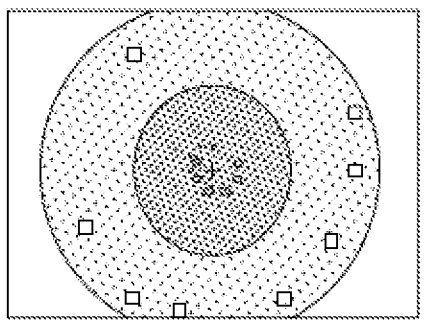
FIGS. 6 to 9 show images taken via the measurement sequence of FIG. 5.
Figure 7:
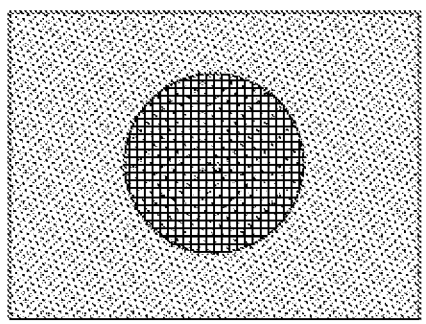
Figure 8:
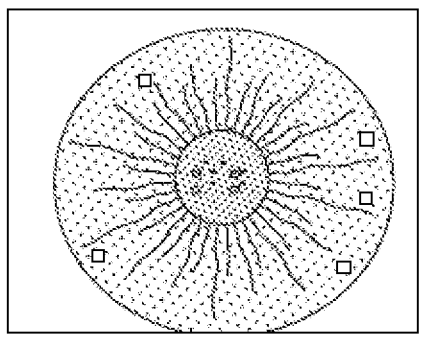
Figure 9:
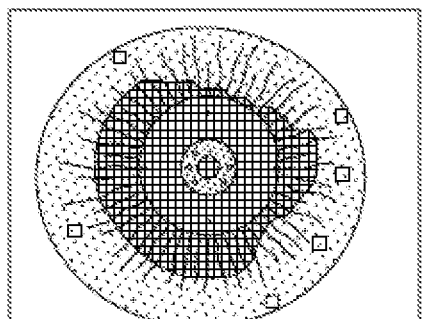

FIGS. 6 to 9 show images taken via the measurement sequence of FIG. 5. FIG. 6 is the iris registration scotopic/mesopic image, which measures the pupil size, position and shape, and the outer iris boundary position and size in low light conditions. The image contains feature detail of the iris. FIG. 7 is the wavefront aberrometer image, which measures light scattered or reflected from a point on the retina. FIG. 8 is the iris registration photopic image, which measures the pupil size, position and shape, and the outer iris boundary position and size in bright light conditions. The image contains feature detail of the iris. FIG. 9 is the corneal topography image.

Returning now to FIG. 4, after the measurements are obtained in step 100, at step 102, possible data fusion relationships are evaluated. These data fusion relationships are data types that are available to multiple images, so that registration between the multiple images may be made by using the commonly available data types. Preferably, a characteristic common to all images is used for data fusion.

In some embodiments, the data may be fused by adjusting data location and orientation. Alternative embodiments may be fused by adjusting data location and limiting eye rotation about the optical axis, often by avoiding gross movement of the patient between measurements (such as by using a common eye measurement location) and by limiting the time between data acquisition for the different measurements. Fortunately, the time sequence for taking multiple measurements on an exemplary multi-modal system may be short, with total image acquisition time for obtaining a plurality of different types of measurements optionally taking less than 30 seconds, often less than 10 seconds, preferably less than 5 seconds, and in some cases taking about 4 seconds or less than a second. Even images/measurements taken with illumination sufficiently different to alter a size of the pupil may be taken at times that are quite close, the differences between the image acquisition times for wavefront and corneal topography, for example, typically being within 1 second, and in exemplary embodiments being within $\frac{1}{5}$ of a second, $\frac{1}{10}$ of a second, or $\frac{1}{30}$ of a second. Under such conditions, rotation of the eye between measurements may be negligible.

In embodiments, rotational adjustments between datasets may be identified using simultaneous pupil shape infatuation (such as may be available from the wavefront data), simultaneous retinal data (optionally including images of vessels or other landmarks obtained during wavefront data acquisition), simultaneous iris data obtained from an co-axial or an off-axis camera, or the like.

Figure 10:
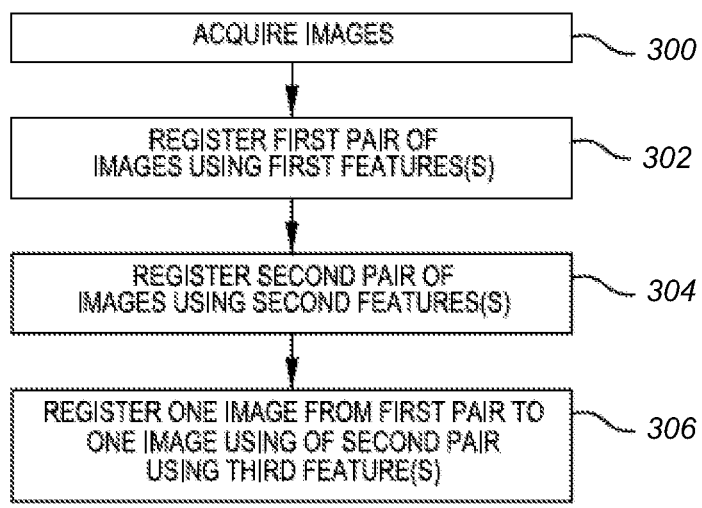
FIG. 10 is a flow chart representing a process for registering multiple datasets that do not have a common characteristic in accordance with an embodiment.

Thus, a number of different systems exist for registration of images to each other when the images have a common characteristic. However, due to the difference measurement principles used to create images, a characteristic common to all images may not be available. It may be sufficient, however, to register images together in subsets, and then register subsets to other subsets until all images are registered to each other. For example, FIG. 10 is a flow chart representing a process for registering multiple datasets that do not have a common characteristic in accordance with an embodiment. At step 300, the images are acquired. At step 302, two images are registered with each other using one or more first features, thus creating a first registered image pair. At step 304, two images, at least one being different from the first set, are registered with each other using one or more second features, thus creating a second registered image pair. At step 306, the two registered image pairs are registered with each other using one image from each pair and one or more third features different from the first features to register the images. After the process in FIG. 10, all images have a determined spatial relationship with each other.

The process of FIG. 10 works particularly well when two datasets are difficult to register with each other because the two datasets do not include common characteristics. In such a situation, an image or a group of images may act as intermediary datasets for the two datasets that are difficult to register together. For example, for the system shown in FIG. 1, as further described below, the corneal topography image is difficult to register directly to the wavefront image because the two images do not contain any common features. The pupil is visible in the wavefront image as the region illuminated, but it is potentially obscured in the corneal topography image by the array of reflected spots or the reflected Placido rings. Furthermore, the wavefront and corneal topography images are taken under different lighting conditions and may be taken at widely different times (hence the eye may be in a different position). Thus, using the process in FIG. 10, the corneal topography image and the wavefront image may each be separately registered to an intermediary dataset, and through those two separate registrations, are ultimately registered to each other. In other words, the corneal topography image is registered to the intermediary dataset, which in turn is registered to the wavefront image. In such a system, the two images that are registered at step 302 include the corneal topography image and the intermediary dataset, and the two images that are registered at step 304 are the wavefront image and the intermediary dataset.

Thus, returning to FIG. 4, a relationship is established at step 104, such as the use of the intermediary dataset described above. At step 106, the first dataset is fused using the relationship, and at step 108, the second dataset is fused using the relationship. After the steps in FIG. 4, all images are fused.

Data that is available from the images differs based upon the image type. With image recognition techniques it is possible to find the position and extent of various features in an image. Turning now to the specific four images captured in FIG. 5, for the iris registration images, features that are available include the position, size and shape of the pupil, the position, size and shape of the outer iris boundary (OIB), salient iris features (landmarks) and other features as are determined to be needed.

In the iris registration images, it is possible, without interference from any of the various reflections (iris illumination sources) to find the pupil position, size and shape accurately. This is facilitated by arrangement of the system components such that the illumination sources are near the optical axis, and thus the reflections are near the center of the pupil, and thus do not interfere with finding the pupil's edge. Information from different landmarks may be correlated, for example, by accurately locating the outer iris boundary and/or iris landmarks relative to the pupil. This may help allow a pupil location to be determined from another image in which the pupil itself is not visible, optionally with greater accuracy than may be provided by relying on an image of the limbus alone (as the limbus may appear as a gradual boundary, rather than having a sharp boundary).

In the corneal topography image, however, it may be advantageous to measure the topography as close to the center as possible. In general the corneal topography projected pattern covers the full pupil, including the center and the edge of the pupil. This pattern may interfere with finding the pupil position, size and shape accurately. Furthermore, the illumination is generally adjusted to optimize the conical topography image for detecting the reflected pattern. This illumination is not necessarily the same, nor optimized for, the detection of the pupil information. Therefore, it may be desirable to find a different feature in the corneal topography image to use for registration information.

It is noted that the strong curvature of the cornea is such that only a limited coverage of the conical, area is often measurable by corneal topography. Usually this coverage includes the pupil and central area, but often does not extend to the outer iris boundary. Thus no projected pattern may be evident in the images near the outer iris boundary. The visible peripheral portion of the iris image included in the corneal topography image may be used for registration, for example, to help accurately locate the pupil (even if the pupil image is not readily seen), to help identify the torsional orientation of the eye about the optical axis of the eye, and/or the like.

Thus it is possible to register the outer iris boundary information that is found in the corneal topography image with that from the iris registration image. The relative position of these two outer iris boundary measurements can be used to determine the correct relative position of the measurement information. Furthermore, the outer iris boundary is a fixed feature in the eye, and does not change with time, or with measurement type.

However, the wavefront aberrometry image generally has no features that correspond to the outer iris boundary. Thus some other feature will often be used to register this image to other images. In wavefront aberrometer, the pupil is back illuminated by the scattering source on the retina, with the retina aperturing the aberrometry data. Thus, the size, shape, and location of the pupil can be accurately determined. The position of the wavefront pupil can thus be registered to the position of the measured pupil from the iris image.

Thus the wavefront data and the corneal topography data can be separately registered to features on the iris registration image. The iris registration image can be treated as a reference image, and both the wavefront data and the corneal topography data can be registered to coordinates that are centered on this image.

The process of FIG. 10 may be used, therefore, to register the wavefront data to the conical topography data, using the iris registration image as the intermediary. There remains at least one further difficulty, however. That is that the pupil might change position as a function of size. Since the illumination is in general different between acquisition of the wavefront and the iris images, it may be that the pupil has changed substantially in size between the two acquisitions.

This issue may be addressed by interpolating the size of the pupil in the wavefront data onto information known about the pupil size from the iris registration information so as to arrive at the position of the pupil for the wavefront. Note that there are two iris images that can be acquired. These differ in the illumination that is provided. The scotopic (or mesopic) image is taken with minimum illumination, preferably in the IR or Near IR wavelengths of light so that the eye does not respond to illumination by changing in size or position. It is usually desirable to maximize the pupil size during the wavefront and scotopic image acquisition.

The other image is the photopic image. It is acquired by first turning on a bright visible (e.g., green) source of illumination, waiting for the eye to respond, and then acquiring an iris image. This results in an image where the pupil is smaller than that of the scotopic image.

As the pupil contracts, it also shifts in position. This relationship is shown in FIG. 11. Pupil P contracts and/or expands with changes in brightness or illumination, with these changes in illumination optionally including changes in the brightness of the object or target being viewed, changes in the ambient light around the viewing target, and the like.

Along with changes in the overall size of pupil P when the eye E is subjected to different viewing conditions, the location of the pupil center C may also change. It should be noted that this change in location of the pupil center may be separate from and in addition to any overall movement of the eye. In other words, even if the eye E were to remain at an overall fixed location in space so that the cornea and the retina of the eye did not move, as the pupil P contracts from a first pupil configuration P to a smaller pupil configuration P, the center C of the pupil may undergo a corresponding change in location to a new pupil center C'. This change in pupil center location is encompassed within the term "pupil center drift" as that term is used herein.

The position and size of the pupil are correlated. That is, as the pupil contracts, it shifts. So with two measurements of the pupil, it is possible to determine this correlation and describe it as a linear shift (which it will be to a good approximation). So for any known or measurement pupil size, from these two images it will be possible to determine a corresponding pupil position. In an embodiment, one of the two images is obtained from a corneal topographer. Alternative embodiments may determine the relationship of pupil size and position using additional images (such as to determine a curved relationship), by continuously or dynamically measuring location and pupil size during changes in illumination, or the like. In addition, in an embodiment, a pupil image is obtained from the corneal topographer, and that image is used to determine the relationship between the pupil size and location.

Thus, with both a photopic image and a scotopic/mesopic image, a relationship may be established between pupil size and position. Thus, using the pupil size obtained in the wavefront image, it is possible to determine the pupil position when the wavefront image was acquired. To this end, the pupil position is described as a linear function of the pupil size by evaluating the pupil size and position from the scotopic/mesopic and photopic images as shown in FIG. 12. Then the corresponding pupil size calculated from the wavefront sensor image is used to "look up" the position of the pupil on this curve. This correlation correctly allows for the appropriate pupil position shift as the eye changes it shape. The offset from the center (or other reference point) of the wavefront image relative to the iris registration image can be used to provide the exact relationship between the various images, taking all the phenomena into account. FIG. 14 shows exemplary pupil positions for a range of pupil sizes, and illustrates an exemplary level of variability over the range of pupil sizes.

Thus, using the above, the relationship established pursuant to step 404 includes: registering the outer iris boundary information that is found in the corneal topography image with that from the iris registration image, and registering the position of the wavefront pupil to the proper position as interpolated from the iris images. These functions are performed, for example, via the registering module 90 and the relationship module 92.

Figure 13:
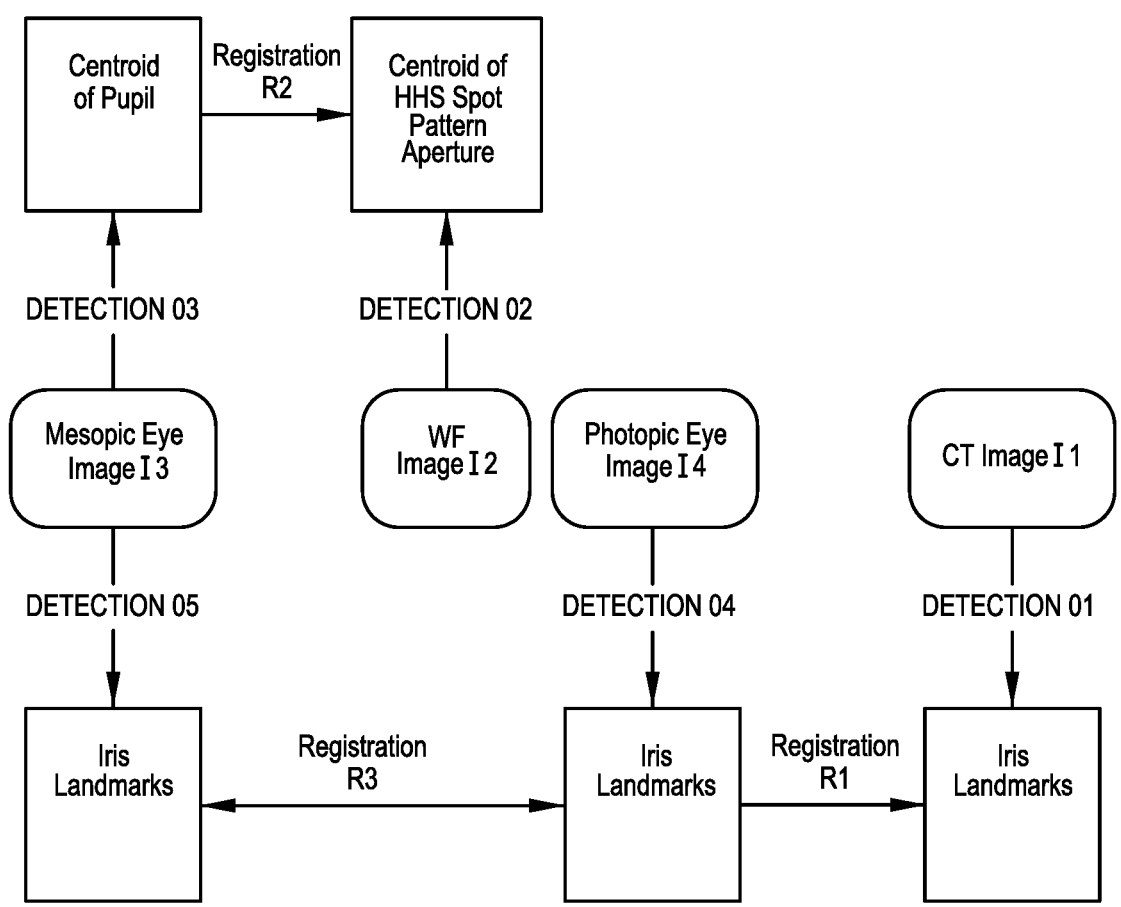
FIG. 13 is a flow chart schematically illustrating a method of indirectly registering optical datasets of an eye, in accordance with many embodiments.

During embodiments of the multi-modal eye diagnosis described herein and shown schematically in FIG. 13, data fusion is optionally achieved when the correct spatial relationship can be established between some or preferably all of the following four datasets:

1. corneal topography image, associated corneal elevation map or data derived from the image or elevation map (such as local gradients of the corneal surface)

2. wavefront image, associated reconstructed ocular wavefront or data derived from the image or wavefront reconstruction (such as the wavefront decomposition into function sets (e.g., Fourier and zonal reconstruction, and Zernike and Taylor polynomial reconstruction)

3. Scotopic eye image or data derived from the scotopic eye image (such as scotopic pupil shape, scotopic pupil size, scotopic pupil centroid position, limbus or outer iris boundary, iris pattern, blood vessel pattern, or artificial landmarks such as flap cut, intrastromal bubble)

4. Photopic eye image or data derived from the photopic eye image (such as photopic pupil shape, photopic pupil size, photopic pupil centroid position, limbus or outer iris boundary, iris pattern, blood vessel pattern, or artificial landmarks such as flap cut, intrastromal bubble)

For embodiments invention disclosed herein, as shown in FIG. 13, registering of the multiple datasets may be used in the following manner. First, the relationship between pupil position and diameter is established from the scotopic and photopic images, as shown in FIG. 12. The pupil size is measured on the wavefront image (along with the relative wavefront offset) by back illuminating the pupil by the scattering source on the retina, with the retina aperturing the aberrometry data (Detections O2 and O3, FIG. 13). Thus, the size, shape, and location of the pupil can be accurately determined. For the pupil size determined from the wavefront measurement, the relative position on the iris images is determined using the previously established relationship of size to position (FIG. 12). Note that the wavefront pupil size is not necessarily between the pupil sizes of the photopic and scotopic images, and may be smaller than the pupil in the photopic image, larger than the pupil in the scotopic image, or the same size as the pupil in either of these images. As long a relationship between size and position is established, the position of the wavefront can be determined or estimated. After the position is determined or estimated, ambiguity as to the position of the images is removed, or at least reduced, and all are thus registered correctly (Registration R2, FIG. 13).

The registration step R1 is now described. First, the iris landmarks are detected from the CT image I1. To do this step, the outer circular boundary C1 of the corneal topography spot pattern is detected. A second circular boundary C2 is chosen to include the limbus border. C1 and C2 are concentric and form a ring of iris structure. A coordinate transformation from cylindrical to Cartesian coordinates is performed—the iris structure ring is unwrapped into an iris structure strip. The iris structure strip is filtered with a Sobel y-gradient filter for edge detection followed by binarization of the image. Additional aspects of determining the center of the limbus and/or pupil may be understood with reference to U.S. Pat. No. 7,044,602 in the name of Chernyak, the full disclosure of which is incorporated herein by reference.

The same steps are performed for the photopic eye image I4. The translational offset between the two limbus centers is now known. A rotational offset between the two images I1, I4 can be computed by correlation of the two iris feature strips with iterations around scale due to elastic deformation of the iris features for constricting/dilating pupils. Thus, the photopic eye image I4 and the CT image I1 can be registered to each other.

The photopic and scotopic eye measurements are registered to each other using known methods, for example via use of iris landmarks (Registration 3). Afterwards, all images and data from the images may be fused.

Wavefront Measurement Systems

In many embodiments, an aberrometer system, for example, a wavefront measurement system, is used to assess the optical aberrations that exist in an eye. Wavefront measurement systems work by measuring the way a wavefront of light passes through the various refractive or focusing components of the eye, such as the cornea and crystalline lens. In one approach, a narrow beam of light is directed upon the retina of an eye and its reflection emerges from the eye. In the case of an ideal eye, the emerging reflection is comprised of uniformly parallel beams of light. However, in the case of a non-ideal eye, the emerging reflection is comprised of non-parallel beams of light due to various optical aberrations throughout the eye. Some wavefront measurements systems use an array of lenses and associated sensors to provide a collection of measurements or gradients, each gradient indicating how much a particular region of the emerging reflection deviates from the ideal parallel path. The measured gradients can then be used to determine a wavefront elevation map having the same gradients as the measured gradients. The wavefront elevation map is a graphical representation of the optical aberrations in the eye, and, with regard to corneal alteration via ablation of the anterior surface of the cornea, is closely correlated with the ablation profile that must be removed to correct the optical aberrations.

Referring now to FIG. 15A, one embodiment of a wavefront measurement system 430 is schematically illustrated in simplified form. In very general terms, the wavefront measurement system 430 is configured to sense local slopes of light exiting the patient's eye. Devices based on the Hartmann-Shack principle generally include a lenslet array to sample light uniformly over an aperture, which is typically the exit pupil of the eye. Thereafter, the local slopes of the exiting light are analyzed so as to reconstruct the wavefront surface or map.

More specifically, the wavefront measurement system 430 includes an image source 432, such as a laser, which projects a source image through optical tissues 434 of an eye (E) so as to form an image 444 upon a surface of a retina (R). The image from the retina (R) is transmitted by the optical system of the eye (e.g., the optical tissues 434) and imaged onto a wavefront sensor 436 by system optics 437. The wavefront sensor 436 communicates signals to a computer system 422' for measurement of the optical errors in the optical tissues 434 and, in many embodiments, determination of a defect-correcting prescription. The computer 422' may include the same or similar hardware as the computer system 17, 19, 22 illustrated in FIGS. 1 and 2. The computer system 422' may be in communication with the computer system 22 that directs the laser surgery system 15, or some or all of the components of the computer system 22, 422' of the wavefront measurement system 430 and the laser surgery system 15 may be combined or separate. If desired, data from the wavefront sensor 436 may be transmitted to the laser computer system 22 via the tangible media 429, via an I/O port, via a networking connection such as an intranet or the Internet, or the like.

The wavefront sensor 436 generally comprises a lenslet array 438 and an image sensor 440. As the image from the retina (R) is transmitted through the optical tissues 434 and imaged onto the wavefront sensor 436, the lenslet array 438 separates the transmitted image into an array of beamlets 442, and (in combination with other optical components of the system) images the separated beamlets 442 on the surface of the sensor 440. The sensor 440 typically comprises a charged coupled device ("CCD") and senses characteristics of these individual beamlets, which can be used to determine the characteristics of an associated region of the optical tissues 434. In particular, where the image 444 comprises a point or small spot of light, a location of a transmitted spot as imaged by a beamlet can directly indicate a local gradient of the light transmitted through the associated region of the optical tissue.

The eye (E) generally defines an anterior orientation (ANT) and a posterior orientation (POS). The image source 432 generally projects an image in a posterior direction through the optical tissues 434 onto the retina (R) as indicated in FIG. 15A. The optical tissues 434 transmit the image 444 from the retina in the anterior direction toward the wavefront sensor 436. The image 444 transmitted through the optical tissues 434 may be distorted by any imperfections in the eye's optical system. Optionally, image source projection optics 446 may be configured or adapted to decrease any distortion of image 444.

In some embodiments, the image source optics 446 may decrease low-order optical errors by compensating for spherical and/or cylindrical errors of the optical tissues 434. High-order optical errors of the optical tissues may also be compensated through the use of an adaptive optic element, such as a deformable mirror (described below). Use of an image source 432 selected to define a point or small spot as the image 444 upon the retina (R) may facilitate the analysis of the data provided by the wavefront sensor 436. Distortion of the image 444 may be limited by transmitting a source image through a central region 449 of the optical tissues 434, which is smaller than a pupil 450, as the central portion of the optical tissues may be less prone to optical errors than a peripheral portion. Regardless of the particular image source structure, it will be generally be beneficial to have a well-defined and accurately formed image 444 on the retina (R).

In some embodiments, the measured wavefront data may be stored in a computer readable medium 429 or a memory of the wavefront sensor system 430 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 451 (FIG. 15A) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of many embodiments will generally be described with reference to sensing of an image 444, it should be understood that a series of wavefront sensor data readings may be taken. For example, a time series of wavefront data readings may help to provide a more accurate overall determination of the ocular tissue aberrations. As the ocular tissues can vary in shape over a period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 430 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from the pupil camera 451. In many embodiments, the pupil camera 451 images the pupil 450 so as to determine a position of the pupil for registration of the wavefront sensor data relative to the optical tissues.

Figure 15B:
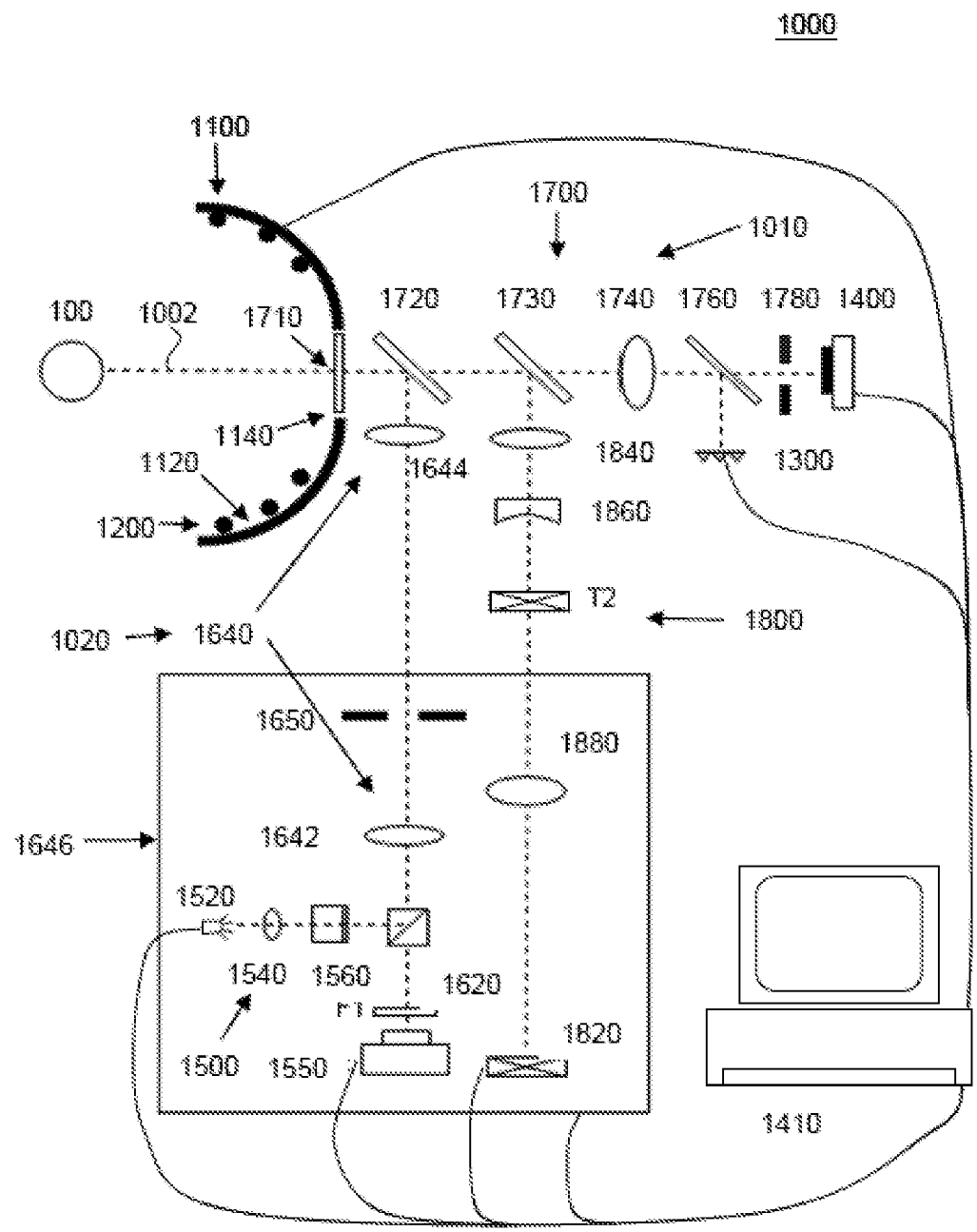
FIG. 15B illustrates another wavefront measurement system in accordance with many embodiments.

An alternative embodiment of a wavefront measurement system is illustrated in FIG. 15B. FIG. 15B shows a system 1000 for measuring aberrations and corneal topography of an eye 100, in accordance with many embodiments. The system 1000 comprises a topographer 1010, an aberrometer or wavefront analyzer 1020, and a processor 1410. The topographer 1010 comprises a structure 1100 having a principal surface 1120 with an opening or aperture 1140 therein; a plurality of first (or peripheral) light sources 1200 provided on the principal surface 1120 of the structure 1100; a plurality of second, or central, light sources 1300 (also sometimes referred to as "Helmholtz light sources"); and a detector, photo detector, or detector array 1400.

The wavefront analyzer 1020 of the system 1000 comprises a third light source 1500 providing a probe beam; a wavefront sensor 1550; and an optical system 1700 disposed along a central axis 1002 passing through the opening or aperture 1140 of the structure 1100. The optical system 1700 comprises a quarter wave plate 1710, a first beam splitter 1720, a second beam splitter 1730, an optical element (e.g., a lens) 1740, a third beamsplitter 1760, and a structure including an aperture 1780. Beneficially, the third light source 1500 includes a lamp 1520, a collimating lens 1540, and light source polarizing beam splitter 1560. The lamp 1520 can be an SLD or a fiber-coupled source that optionally includes an optical coherence tomographer (OCT). Wavefront analyzer 1020 further comprises a polarizing beam splitter 1620; an adjustable telescope 1640 comprising a first optical element (e.g., lens) 1642 and a second optical element (e.g., lens) 1644 and a movable stage or platform 1646; and a dynamic-range limiting aperture 1650 for limiting a dynamic range of light provided to wavefront sensor 1550 so as to preclude data ambiguity. It will be appreciated by those of skill in the art that the lenses 1642, 1644, or any of the other lenses discussed herein, can be replaced or supplemented by another type of converging or diverging optical element, such as a diffractive optical element. Beneficially, the system 1000 further comprises a fixation target system 1800, comprising light source 1820 and lenses 1840, 1860, and 1880. The structure and use of the system 1000 of FIG. 15B are more fully described in U.S. Patent Publication No. 2009/0161090 A1, the full disclosure of which is incorporated herein by reference. Another exemplary wavefront system is described in U.S. Pat. No. 6,550,917, the full disclosure of which is incorporated herein by reference.

Figure 16:
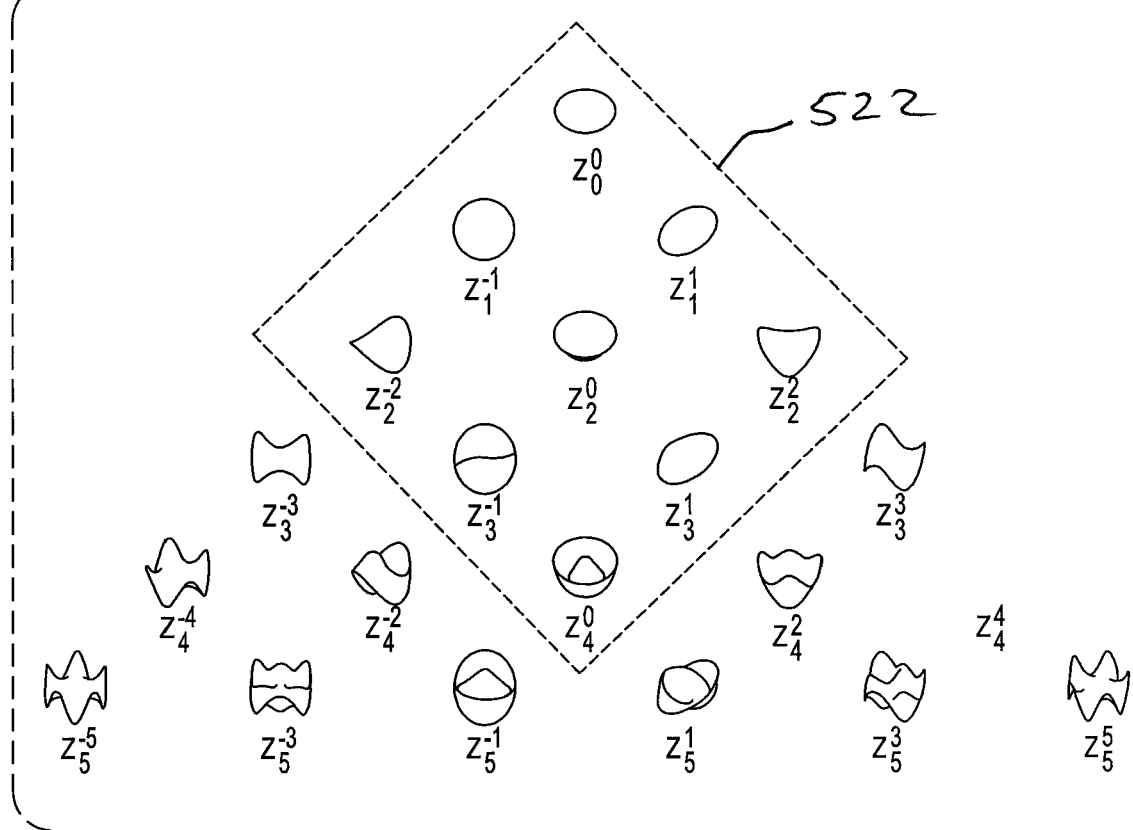
FIG. 16 illustrates Zernike polynomial shapes.

Although a wavefront elevation map may be created from optical gradient data in any number of ways, wavefront elevation map creation by way of fitting the gradient data to a combination of one or more Zernike polynomials is one commonly used approach. Zernike polynomials represent a particularly beneficial form of a mathematical series expansion for modeling the wavefront elevation map. FIG. 16 illustrates the shapes of a subset of Zernike polynomials, which are a function of normalized radius and angle for a given order and frequency. In many embodiments, Zernike polynomial sets including terms 0 through 6th order or 0 through 10th order are used. The coefficients $a_n$ for each Zernike polynomial $Z_n$ may, for example, be determined using a standard least-squares fit technique. In practice, the number of Zernike polynomial coefficients used may be limited (for example, to about 28 coefficients).

Even Zernike Polynomials:

$$Z_n^m(\rho,\theta)=R_n^m(\rho)\cos(m\theta)$$

Odd Zernike Polynomials:

$$Z_n^{-m}(\rho,\theta)=R_n^m(\rho)\sin(m\theta)$$

where:

m and n are nonnegative integers with n≥m,

θ is the azimuthal angle in radians,

ρ is the normalized radial distance, and $$R_n^m(\rho) = \sum_{k=0}^{(n-m)/2} \frac{(-1)^k(n-k)!}{k!((n+m)/2-k)!((n-m)/2-k)!}\rho^{n-2k} \text{ (if } n\text{-}m \text{ is even)}$$

$$R_n^m(\rho) = 0 \text{ (if } n\text{-}m \text{ is odd)}$$

Where an array of Zernike coefficients has been determined, the wavefront elevation map can be created. Scaling the Zernike polynomials by their coefficients and summing the scaled Zernike polynomials allows a wavefront elevation map to be calculated, and in some cases, may very accurately reconstruct a wavefront elevation map.

An additional benefit to wavefront elevation reconstruction by way of Zernike polynomials relates to the correspondence between certain Zernike polynomial shapes and commonly known optical aberrations, such as between Zernike polynomial for defocus (n=2, f=0) and nearsightedness or farsightedness, as well as the Zernike polynomial shapes for astigmatism (n=2, f=±2). The low-order aberrations of defocus and astigmatism account for a vast majority of the optical errors present in a typical eye.

Figure 17A:
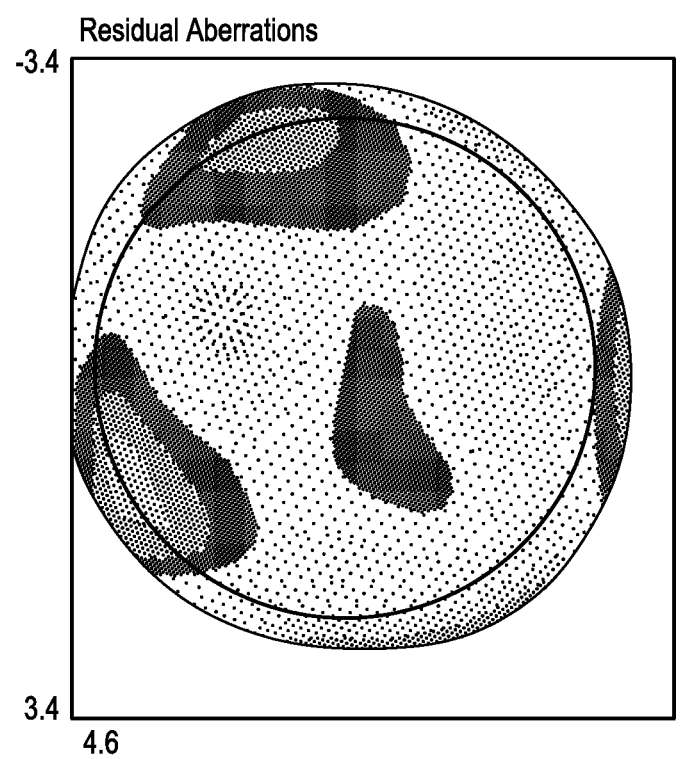
FIG. 17A illustrates a modal approximation of a wavefront surface.

However, high-order aberrations corresponding to high-order Zernike polynomials do exist to a significant extent, and are associated with vision errors such as difficulty seeing at night, glare, halos, blurring, starburst patterns, double vision, or the like. Accordingly, improved vision correction may result by way of improved correction of high-order aberrations. FIG. 17A illustrates a modal approximation of an example wavefront surface.

Figure 17B:
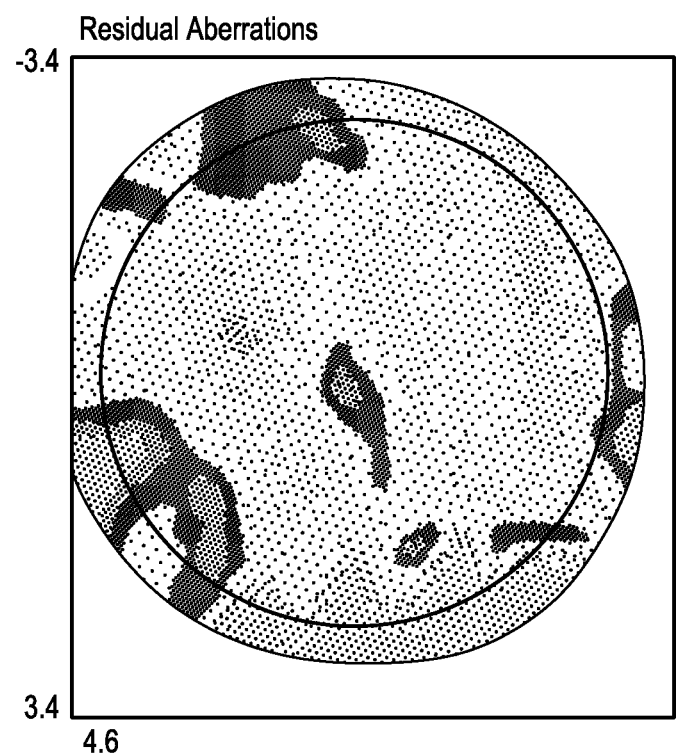
FIG. 17B illustrates a zonal approximation of a wavefront surface.

Wavefront elevation maps can also be created for a wavefront measurement by using a zonal approximation. Exemplary approaches that can be used to approximate a wavefront surface using a zonal approach are disclosed in U.S. Pat. No. 7,175,278, entitled "Wavefront Reconstruction Using Fourier Transformation and Direct Integration," filed Jun. 20, 2003; and in U.S. Pat. No. 7,168,807, entitled "Interactive Fourier Reconstruction for Laser Surgery and Other Optical Application," filed Jun. 17, 2004; the full disclosures of which are hereby incorporated herein by reference. Such zonal approximations can be used to more accurately approximate wavefront surfaces having locally complex shapes as compared to some modal approximation approaches (e.g., fitting $6^{th}$ order Zernike polynomials). FIG. 17B illustrates a zonal approximation of an example wavefront surface, which includes locally complex shapes.

A zonal approximation can be processed to generate values for commonly known optical aberrations (e.g., such as discussed above). For example, the methods disclosed in U.S. Pat. No. 7,331,674, entitled "Calculating Zernike Coefficients from Fourier Coefficients," filed Sep. 2, 2005, the entire disclosure of which is hereby incorporated herein by reference, can be used to calculate Zernike Coefficients for a modal approximation of the zonal approximation (e.g., terms for sphere, cylinder, coma, and/or other terms).

Optical Diagnosis and Correction Selection

Figure 18:
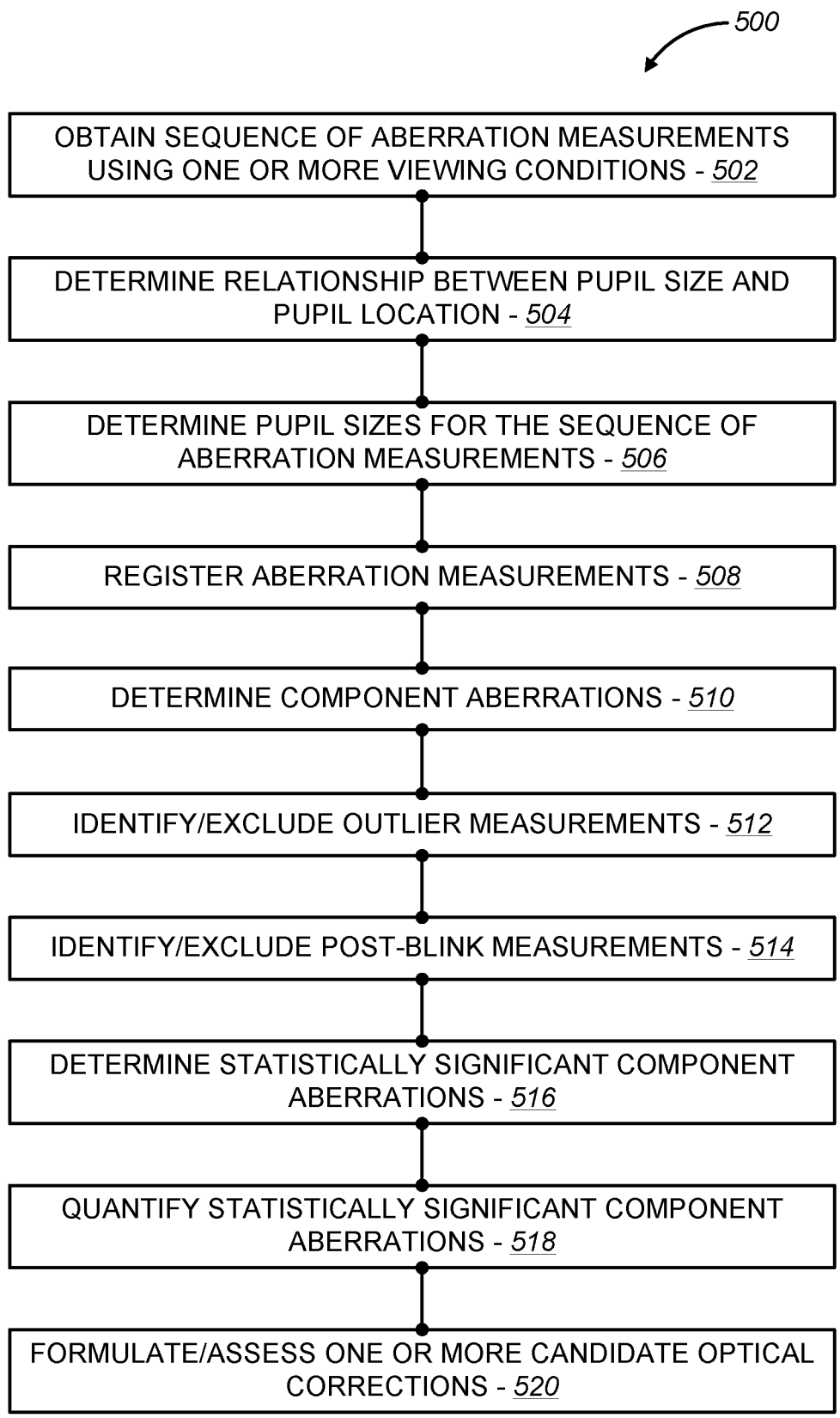
FIG. 18 shows method steps for optically diagnosing an eye using a sequence of aberration measurements, in accordance with many embodiments.

FIG. 18 shows steps of a method 500 for diagnosing optical aberrations of an eye, and formulating and assessing one or more candidate optical corrections, in accordance with many embodiments. The method can be used to determine statistically-significant aberrations of the eye for one or more viewing conditions. The identified statistically significant aberrations can be quantified and used to formulate one or more candidate corrections, the performance of which can be assessed relative to the aberrations of the eye for one or more viewing conditions.

In step 502, a sequence of aberration measurements is obtained. In many embodiments, the measurement sequence is obtained by using a wavefront system such as described above. The sequence of measurements can be obtained during a single examination period, and can also be obtained over two or more examination periods. In many embodiments, the viewing conditions are varied and/or changed while the sequence of measurements is obtained. For example, a plurality of viewing distances and/or illumination levels can be used as described in U.S. Pat. No. 7,513,620, the full disclosure of which is hereby incorporated herein by reference. Different portions of the sequence of measurements can be dedicated to different viewing conditions. And each portion can include a sufficient number of measurements to establish a sufficient basis from which to determine a suitable number of component aberrations for the viewing condition, which can include both low-order aberrations and a suitable number of high-order aberrations for the desired accuracy of the optical diagnosis. As will be described in more detail below, varying the viewing conditions enables the determination of the aberrations of the eye for the varied viewing conditions. And the determined aberrations for the varied viewing conditions can be used to formulate/assess an optical correction for the eye.

For example, FIG. 19A illustrates a sequence of accommodation measurements (via measured refraction) and pupil radius measurements of a young eye. The measurement sequence begins with the eye viewing a far target. The viewing target is then changed to be a near target, thereby causing the eye to accommodate as illustrated by the change in the measured refraction. Finally, the viewing target is then changed back to be a far target, thereby resulting in the illustrated change in the measured refraction. During the measurement sequence, the pupil radius is also measured.

Steps 504, 506, 508 are used to register the aberration measurements with a fixed reference of the eye. This registration ensures that during subsequent processing the individual aberration measurements can be more readily compared due to the common reference frame. In step 504, a relationship for the eye between pupil size and pupil location is determined. The pupil size/location relationship (e.g., as illustrated in FIG. 12 and FIG. 14) can be determined as described above. In step 506, each measurement of the sequence of aberration measurements is processed to determine the pupil size for the measurement. The pupil size for the measurement (e.g., as illustrated in FIG. 7) can be determined as described above. Once the pupil size for the measurement is determined, the pupil location for the measurement can be determined using the above-described relationship. And the aberration measurement can be registered using the determined pupil location.

In step 510, component aberrations are determined for each measurement of the sequence of measurements. In many embodiments, each measurement of the sequence of measurements is used to generate a wavefront elevation map for the measurement. As described above, the component aberrations can be determined by fitting a combination of one or more Zernike polynomials to the measurement gradient data. As a result, sequences of Zernike polynomial coefficients corresponding to individual component aberrations of the sequence of measured aberrations are generated. The variation of any particular Zernike polynomial during the sequence of measurements (or portion of the sequence) can then be observed and/or quantified.

In step 512, any outlier measurements can be identified so that they can be excluded from subsequent processing. For example, FIG. 19B illustrates outlier accommodation measurements caused by blinks and partial blinks. Such blinks and partial blinks interfere with one or more wavefront measurements, as illustrated by the abrupt change in the measured pupil radius and the measured refraction, thereby producing outlier measurements. By excluding such outlier measurements, a qualified sequence of accommodation measurements can be obtained such as illustrated in FIG. 19C.

Data qualification for measurements (e.g., accommodation measurements, aberration measurements) can be based on physically reasonable limits. For example, qualified data can be limited to measurements in which the pupil center is well within the sensor field of view. As pupil radii are seldom less than 1 mm, blinks can be identified by checking the sequence of pupil radius measurements for pupil radii of less than a predetermined value (e.g., less than 0.5 mm). Partial blinks and field of view errors can be identified by checking the magnitude of the rate of change of the pupil radii for rates of change greater than a predetermined rate (e.g., greater than 3 mm/sec). As pupil radii will typically change by more than 0.5 mm when accommodating, a pupil radius for a near viewing condition and a pupil radius for a far viewing condition can be required to differ by more than a predetermined amount (e.g., 0.5 mm). Some outlier sphere equivalent refraction (SEQ) can be identified due to being outside a predetermined range such as a reasonably expected range (e.g., less than −15 D or greater than +15 D). Some outlier SEQ measurements can be identified by checking to see if the magnitude of the rate of change of SEQ is greater than a predetermined rate (e.g., greater than 25 D per second). Proper fixation on a far viewing target can be checked by comparing the resulting far SEQ to the manifest refraction of the eye. If the magnitude of the difference between the far SEQ and the manifest refraction is greater than a predetermined value (e.g., greater than 1.5 D), the far target may have been out of focus to the subject. Proper fixation on a near viewing target can be checked by comparing the resulting near SEQ to the manifest refraction of the eye minus the stimulus. If the magnitude of the difference between the near SEQ and the manifest refraction minus the stimulus is greater than a predetermined value (e.g., greater than 2 D), the near target may have been out of focus to the subject, Data qualification for measurements can also be based upon detecting an outlier measurements) that has a transitory high-order aberration(s) by identifying an aberration measurement having an elevated Wavefront Fit Error (WFFE) as compared to other aberration measurements of the sequence of measurements. As transitory higher-order aberrations may not be as accurately approximated by a modal approximation approach, and as a zonal approximation approach may more accurately approximate such transitory higher-order aberrations, an elevated difference between a modal approximation and a zonal approximation for the same measurement may be indicative of the presence of such a transitory higher-order aberration.

A gradient fit error ($\beta_{fit}$) can be scaled by the measurement size at the eye (d) to approximate the WFFE.

$$WFFE \approx \beta_{fit} d$$

The gradient fit error ($\beta_{fit}$) can be calculated from a wavefront measurement and a modal reconstruction of the wavefront measurement. In a modal reconstruction of the wavefront measurement, the wavefront surface is expressed in terms of a polynomial expansion (e.g., Zernike polynomials, Taylor polynomials).

$$w(x, y) = \sum_{m=1}^{M} C_m P_m(x, y)$$

The measured slopes are fit to the derivatives of the basis set.

$$(\partial w / \partial x)_k = \sum_{m=2}^{M} C_m \frac{\partial P_m}{\partial x}$$

$$(\partial w/\partial y)_k = \sum_{m=2}^{M} C_m \frac{\partial P_m}{\partial y}$$

The gradient fit error ($\beta_{fit}$) can then be calculated using the aberration measurement and the modal reconstruction.

$$\beta_{fit}^2 = \sum_k \left(\beta_k^x - \sum_{m=2}^{M} C_m \frac{\partial P_m}{\partial x}\right)^2 + \sum_k \left(\beta_k^y - \sum_{m=2}^{M} C_m \frac{\partial P_m}{\partial y}\right)^2$$

$$\beta_{fit}^2 = \frac{1}{N}\sum_k \left(\beta_k^x - \sum_{m=2}^{M} C_m \frac{\partial P_m(x_k, y_k)}{\partial x}\right)^2 +$$

$$\frac{1}{N}\sum_k \left(\beta_k^y - \sum_{m=2}^{M} C_m \frac{\partial P_m(x_k, y_k)}{\partial y}\right)^2$$

Wherein $\beta_k^x$ and $\beta_k^y$ are measured slope values of the aberration measurement.

Figure 20A:
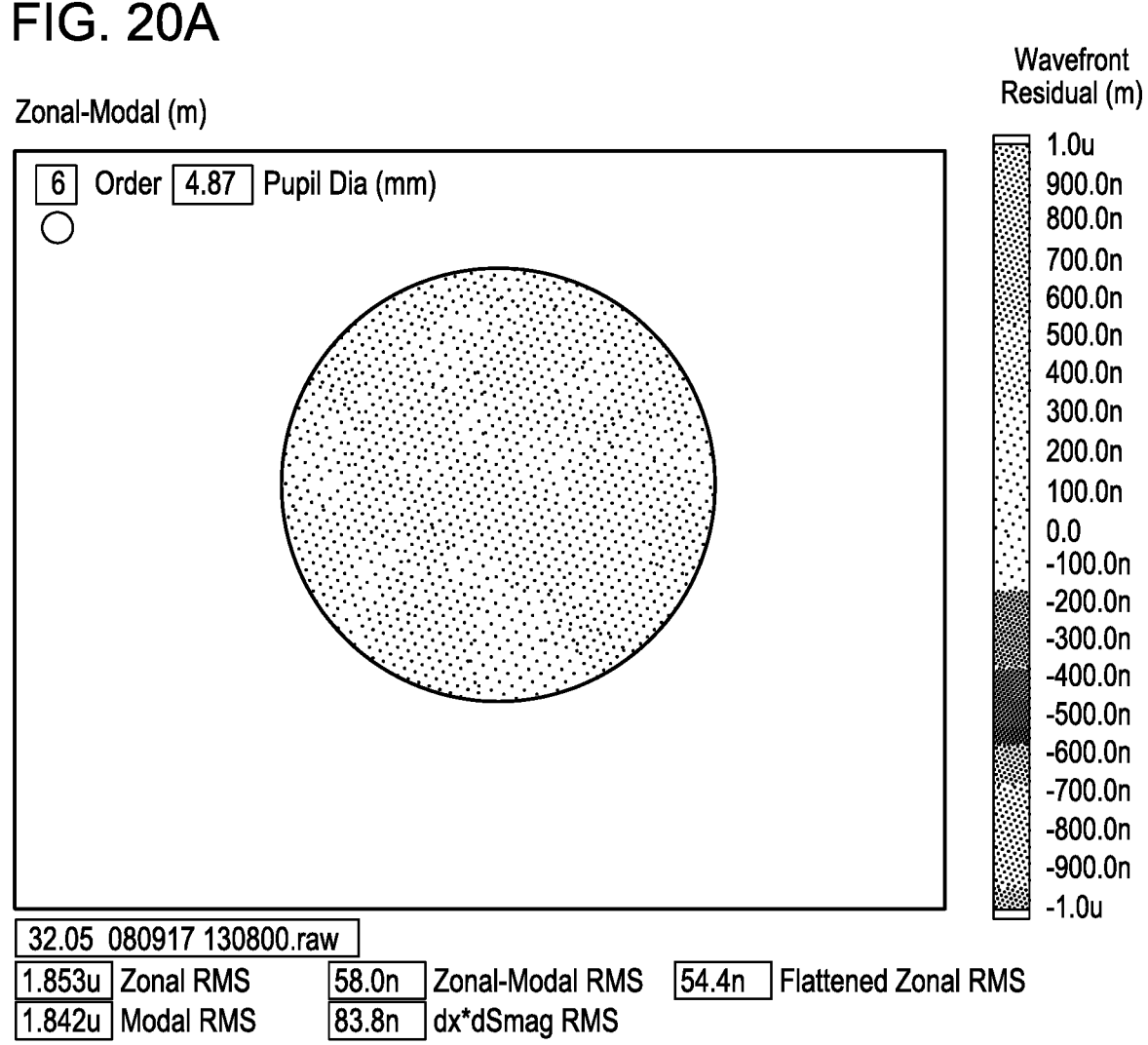
FIG. 20A shows a difference between a zonal approximation of a wavefront surface and a modal approximation of a wavefront surface for a typical wavefront measurement that is closely approximated by a modal approximation, in accordance with many embodiments.
Figure 20B:
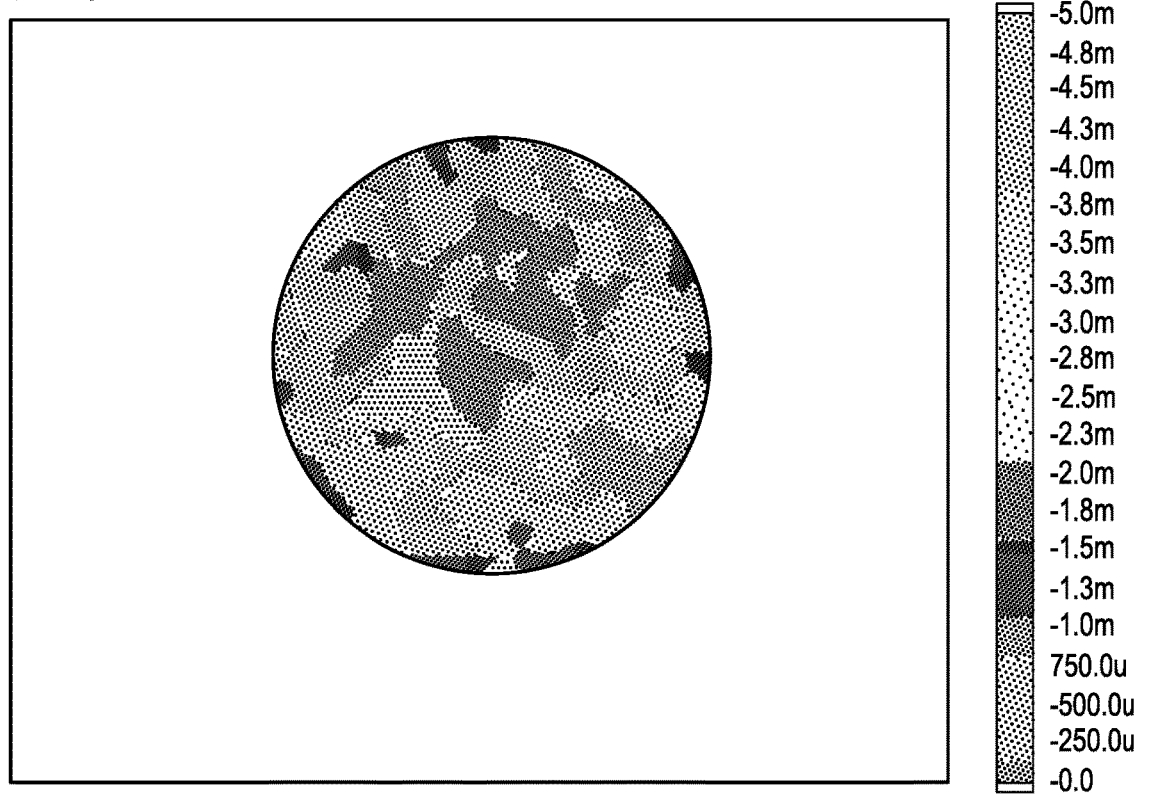
FIG. 20B is a slope residual map showing low residual fit error between a modal approximation of the wavefront surface of the wavefront measurement of FIG. 20A, in accordance with many embodiments.

While a non-outlier aberration measurement may produce modal and zonal approximations that correlate well, an outlier aberration measurement may produce modal and zonal approximations that deviate significantly. For example, FIG. 20A shows a difference between a zonal approximation of a wavefront surface and a modal approximation of a wavefront surface for a typical wavefront measurement that is closely approximated by a modal approximation. In the wavefront measurement of FIG. 20A, the total zonal root mean square (RMS) error is 1.853 μm, the total modal RMS is 1.842 μm, the residual zonal-modal RMS error is 0.058 μm, and the WFFE is 0.0838 μm. Likewise, FIG. 20B is a slope residual map showing low residual fit error between a modal approximation of the wavefront surface of the wavefront measurement of FIG. 20A. In contrast, FIG. 20C shows a difference between a zonal approximation of a wavefront surface and a $6^{th}$ order modal approximation of a wavefront surface for a wavefront measurement influenced by a tear film. In the wavefront measurement of FIG. 20C, the total zonal RMS error is 1.276 μm, the total modal RMS is 1.220 μm, the residual zonal-modal error is 0.338 μm, and the WFFE is 0.551 μm.

Outliner aberration measurements can also be identified by statistically evaluating one or more sequences of component aberrations (e.g., one or more sequences of Zernike polynomial coefficients corresponding to individual component aberrations of the sequence of measured aberrations) using known statistical methods. For example, a blink may be identified by detecting a statistically-significant variation in a sequence of Zernike coefficients corresponding to a stable lower-order aberration.

In step 514, one or more post-blink measurements can be identified for possible exclusion from subsequence processing. A post-blink measurement is a measurement taken immediately following a blink of an eye (e.g., less than one-quarter second following the end of a blink). Post-blink measurements may exhibit transitory aberrations arising from the blink. For example, blink induced transitory changes in the tear film may induce such transitory aberrations. As such, exclusion of post-blink measurements from subsequent processing can be used to prevent such transitory aberrations from influencing the results of the optical diagnosis.

Figure 21:
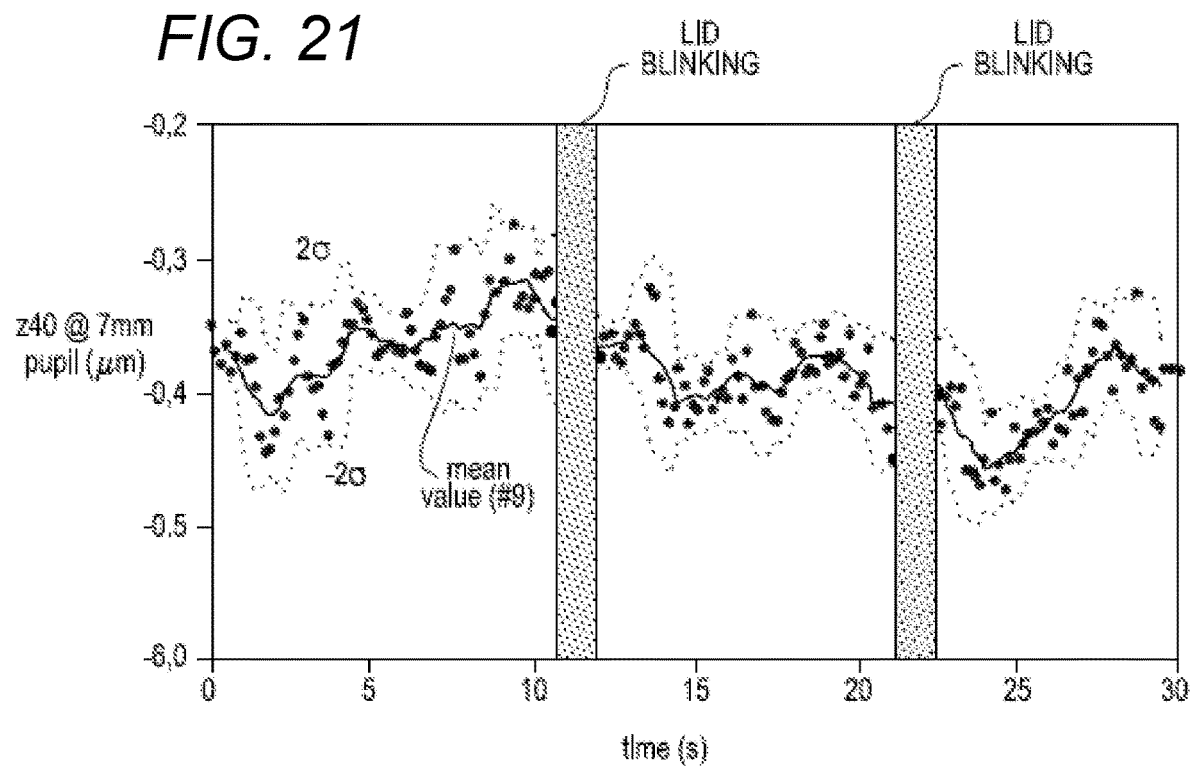
FIG. 21 illustrates an exemplary variation over time of a sequence of coefficients corresponding to a component aberration of a sequence of aberration measurements, in accordance with many embodiments.

In step 516, statistically-significant component aberrations are determined. Each sequence of component aberrations can be analyzed using known statistical methods to determine whether that particular component aberration is statistically significant. Often, low-order component aberrations will be statistically significant. And the question comes down to whether particular high-order aberrations are statistically significant. As such, the analysis can focus on selected high-order aberrations, for example, third-order through eighth-order aberrations. For example, FIG. 21 illustrates an exemplary sequence of values for an eighth-order component aberration (Zernike 40). A statistically-significant component aberration exhibits relative stability over a sequence of measurements for a particular viewing condition.

In step 518, the statistically-significant component aberrations identified as describe above are quantified. As illustrated in FIG. 21, a component aberration may exhibit some level of variability over time and yet be relatively stable for the viewing condition involved. For example, the sequence of determined coefficients for the Zernike 40 aberration shown in FIG. 21 can be processed to generate a single representative number for the aberration component (e.g., by averaging the coefficients of non-excluded measurements for a particular viewing condition, by using a least-squares-fit method).

In step 520, one or more candidate optical corrections are formulated and assessed relative to one or more viewing conditions. A candidate optical correction can be formulated in a variety of ways. One approach involves formulating an optical correction that partially or fully addresses one or more, and possibly all, of the statistically relevant aberrations of the eye that were measured, identified, and quantified as described above. Such an optical correction can be assembled by selecting coefficients for component optical corrections that correspond to the statistically-significant component aberrations. For example, if a particular component aberration varies from a first value to a second value over a range of viewing conditions, a value intermediate to the first and second values can be selected for that particular correction component of the candidate optical correction. Other approaches for selecting a candidate optical correction can be used. For example, a previously identified defect-correcting prescription can be simply provided as a starting point. The defect-correcting prescription can also be identified using methods described in numerous patents, patent publications, and patent applications assigned to Advanced Medical Optics, Inc., including, for example, U.S. Pat. Nos. 6,280,435; 6,663,619; 7,261,412; 7,293,873; 7,320,517; 7,387,387; 7,413,566; 7,434,936; 7,475,986; 7,478,907; and U.S. Pat. Publication Nos. 2004/0054356 A1; US 2005/0261752 A1; 2008/0291395 A1; 2009/0000628 A1; and 2009/0036981 A1; the entire disclosures of which are hereby incorporated by reference herein.

A candidate optical correction can also be formulated corresponding to a selected group of Zernike coefficients suitable for the corrective technique to be employed (e.g., corrective glasses, laser-eye surgery, contacts, etc.). For example, FIG. 16 shows a group of coefficients 522 that includes a particular symmetrical selection of Zernike polynomials corresponding to component that may be suitable for a particular correction. With corrective techniques involving relative movement between the eye and the corrective means (e.g., glasses, contacts), a group of coefficients targeting mostly lower-order aberrations may be suitable. For laser eye surgery, the addition of more higher-order aberrations may be suitable.

The candidate optical correction can then be assessed relative to one or more viewing conditions. For example, a merit function can be used to assess the candidate correction.

$$MF = \sum_{k} I_k \sum_{pupil} [W_k(x, y) - R(x, y)]^2 \qquad \text{Equation (1)}$$

Where:
k indicates a particular measurement of the sequence of aberration measurements;
$I_k$ is a factor that can be used weight particular measurements (e.g., can be zero to
eliminate outlier measurements, post-blink measurements, etc.)
$W_k(x,y)$ is a particular wavefront measurement; and
R(x,y) is the candidate correction as defined by equation (2) below $$R(x,y)=S(x^2+y^2)/2+C[(x \cos \phi)^2+(y \sin \phi)^2]/2 \qquad \text{Equation (2)}$$

Equation (1) sums the differences between each wavefront measurement and the candidate correction over the pupil to limit the assessment to the active part of the eye for that measurement. The relative performance of candidate corrections can be compared by using Equation (1) with a fixed set of measurements used for $W_k(x,y)$ for each candidate correction assessed.

Variations of Equation (1) can also be used to assess one or more candidate optical corrections. For example, instead of using actual aberration measurements for $W_k(x,y)$, a combination of the statistically-significant component aberrations for particular viewing conditions can be used. Additionally, $I_k$ can be used to weight a particular viewing condition to reflect a level of importance associated with the viewing condition. For example, a 0.4 factor can be used to weight a daytime viewing condition, a 0.4 factor can be used to weight a "work" viewing condition, and a 0.2 factor can be used to weight a "sport" viewing condition. Thus, one or more candidate corrections can be assessed (and compared) relative to any selected number of viewing conditions. And the viewing conditions can be weighted according to relative importance during the assessment.

The above-described approaches can also be used to create optical corrections customized for an activity. For example, a correction can be determined for use at night. Likewise, a correction can be determined for use during the day. The daytime and nighttime corrections can be incorporated into various means for applying a correction including, for example, spectacles and/or contact lenses.

The above-described approaches can also be customized for laser-assisted in situ keratomileusis (LASIK) eye surgery and Photorefractive keratectomy (PRK) eye surgery. For example, known error terms can be included (e.g., healing response, laser alignment to eye, tracking error, etc.).

Configuring Contact Lenses

Figure 22:
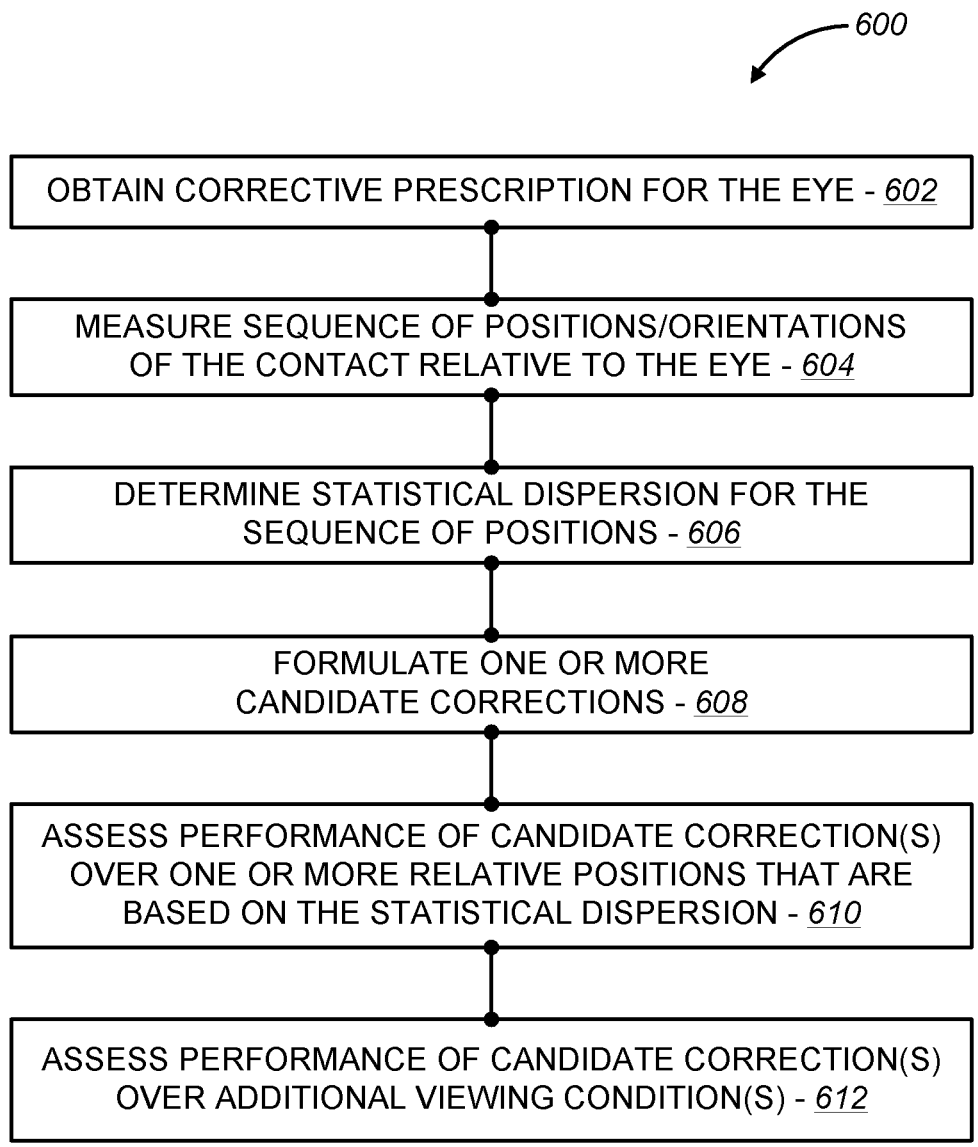
FIG. 22 shows method steps for configuring a contact lens, in accordance with many embodiments.

FIG. 22 shows steps of a method 600 for configuring a contact lens, in accordance with many embodiments. The method can be used to determine which high-order corrections to incorporate into the contact lens.

In step 602, a corrective prescription for the eye is obtained. For example, the corrective prescription can be obtained using any of the approaches described or referenced above with respect to the candidate optical correction.

In step 604, a sequence of positions and orientations of a contact (disposed in an eye) relative to the eye are measured. For each measurement, the position and orientation of the eye can be tracked as described above. Reference marks can be added to the contact and the position and orientation of the reference marks tracked relative to the eye so as to provide both relative position and relative orientation measurements between the contact and the eye.

The sequence of relative positions and orientations are analyzed in step 606 to determine statistical dispersions for the sequence of relative positions and orientations. For example, a mean relative position and a mean relative orientation can be determined. And the standard deviation for both the relative positions and the relative orientations can be determined.

In step 608, one or more candidate corrections are formulated. In many embodiments, which high-order corrections to include into a candidate correction are determined in response to the amount of statistical dispersion observed in the relative positions and/or the relative orientations. For example, where the relative positions vary by more than 1 mm, third-order and higher corrections can be excluded from, the candidate correction (e.g., only first and second-order corrections are included). And where the relative positions vary by between 0.5 to 1.0 mm, for example, fourth-order and higher corrections can be excluded. And where the relative positions vary less than 0.5 mm, for example, seventh-order and higher corrections can be excluded. Other approaches can be used for formulating a candidate correction, for example, any of the above-described or references approaches.

In step 610, the performance of the one or more candidate corrections is assessed over one or more relative positions and/or relative orientations based on the observed statistical dispersion of the relative positions and/or the relative orientations. Equation (1) set forth above can be used to perform this assessment by inducing a relative shift in position and/or orientation of $W_k(x,y)$ or R(x,y) (preferably R(x,y) to reduce the amount of computations required) via a suitable imposed translation or rotation for each relative position and/or relative orientation assessed.

Step 612 can be used to assess the performance of the one or more candidate corrections relative to one or more additional viewing conditions. Step 612 can be accomplished using the approach of step 610 described above, but in which the $W_k(x,y)$ is selected to reflect the viewing condition being assessed.

The method 600 can be adapted for use with other types of vision corrections. For example, the direction that an eye looks through a spectacle lens varies. Such a variation can be tracked and used to configure the spectacle lens so as to best reflect the observed variation.

While exemplary embodiments have been described herein in some detail, for clarity of understanding and by way of example, a variety of adaptations, changes, and modifications will be clear to those of skill in the art. For example, a variety of wavefront sensor systems from a variety of alternative suppliers may be employed. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An optical diagnostic system for an eye having a pupil, the system comprising:
  a sensing device for measuring aberrations of the eye for each of a sequence of aberration measurements of the eye; and
  a computer coupled with the sensing device, the computer comprising a processor and a computer readable medium comprising instructions executable by the processor to identify an outlier aberration measurement of the sequence of aberration measurements of the eye and exclude the outlier aberration measurement from the sequence of aberration measurements to produce a qualified sequence of aberration measurements.

2. The system of claim 1, wherein the instructions are executable by the processor to formulate an optical correction for the eye in response to the qualified sequence of aberration measurements.

3. The system of claim 1, wherein the sensing device comprises a wavefront sensor.

4. The system of claim 1, wherein the sensing device determines a plurality of refractive coefficients corresponding to sensed aberrations of the eye for each measurement of the sequence of aberration measurements.

5. The system of claim 1, wherein the instructions are executable by the processor to determine a plurality of refractive coefficients corresponding to sensed aberrations of the eye for each measurement of the sequence of measurements.

6. The system of claim 1, wherein the instructions are executable by the processor to register the sequence of aberration measurements by using at least one of a location of the eye or an orientation of the eye.

7. The system of claim 6, further comprising a measurement device coupled with an input of the computer to measure a position of at least one of a natural feature of the eye or an artificial reference mark added to the eye so as to generate eye orientation data.

8. The system of claim 1, wherein identifying an outlier aberration measurement comprises analyzing a component aberration of the sequence of aberration measurements.

9. The system of claim 1, wherein identifying an outlier aberration measurement comprises identifying a post-blink aberration measurement that follows a blink of the eye by less than a pre-determined amount of time.

10. The system of claim 9, wherein identifying a post-blink aberration measurement comprises at least one of detecting a radius of the pupil that is less than a predetermined value, detecting a rate of change of a radius of the pupil that is greater than a predetermined rate, or detecting a radius of the pupil that is inconsistent with a linear interpolation based on nearby qualified radius measurements of the pupil.

11. The system of claim 1, wherein identifying an outlier aberration measurement comprises identifying a sphere equivalent refraction (SEQ) of the eye that is outside a predetermined range.

12. The system of claim 1, wherein identifying an outlier aberration measurement comprises identifying a rate of change of SEQ of the eye that is greater than a predetermined rate.

13. The system of claim 1, wherein identifying an outlier aberration measurement comprises identifying a SEQ of the eye for a measurement corresponding to viewing a far viewing target that differs from a manifest refraction of the eye by more than a predetermined value.

14. The system of claim 1, wherein identifying an outlier aberration measurement comprises identifying a SEQ of the eye for a measurement corresponding to viewing a near viewing target that differs from a manifest refraction of the eye minus a stimulus corresponding to the near viewing target by more than a predetermined value.

15. The system of claim 1, wherein identifying an outlier aberration measurement comprises identifying a measurement having a first wavefront fit error (WFFE) for the eye that exceeds a second WFFE for the eye by more than a predetermined amount.

16. The system of claim 1, further comprising an input receiving data from which a plurality of viewing conditions imposed upon the eye during the sequence of aberrations measurements can be determined, and wherein the instructions are executable by the processor to determine the plurality of viewing conditions and store the plurality of viewing conditions in the computer readable medium.

17. The system of claim 16, wherein the plurality of viewing conditions comprise different illumination levels.

18. The system of claim 17, wherein the illumination levels comprise an daytime illumination level and a nighttime illumination level.

19. The system of claim 16, wherein the plurality of viewing conditions comprise a first viewing condition and a second viewing condition, wherein a change from the first to the second viewing condition induces an accommodation of the eye.

20. The system of claim 16, wherein the instructions are executable by the processor to quantify statistically-significant component aberrations of the eye for a plurality of the viewing conditions.

21. The system of claim 20, wherein the instructions are executable by the processor to determine a performance of a candidate optical correction for the eye over a plurality of the viewing conditions by using a merit function that assesses the candidate optical correction relative to the plurality of the viewing conditions.

22. The system of claim 21, wherein the merit function comprises at least one factor to account for a relative importance of at least one of the plurality of viewing conditions.

23. The system of claim 21, wherein determining a performance of a candidate optical correction for the eye comprises assessing the candidate optical correction relative to the quantified component aberrations for each of the plurality of viewing conditions over a portion of the eye corresponding to a pupil size of the eye and a pupil location of the eye for the viewing condition.

24. The system of claim 16, wherein the instructions are executable by the processor to:
  determine a performance of each of a plurality of candidate optical corrections for the eye over each of a plurality of the viewing conditions; and
  determine a prescriptive optical correction for the eye in response to the determined performances for the candidate optical corrections.

* * * * *